United States Patent
Biss et al.

(10) Patent No.: US 8,720,783 B2
(45) Date of Patent: *May 13, 2014

(54) DEVICE AND SYSTEM FOR PROCESSING IMAGE DATA REPRESENTING BAR CODES

(71) Applicant: Hand Held Products, Inc. doing business as Honeywell Scanning and Mobility, Fort Mill, SC (US)

(72) Inventors: Charles E. Biss, Auburn, NY (US); William H. Havens, Syracuse, NY (US); Michael D. Robinson, Weedsport, NY (US); Paul Balschweit, Auburn, NY (US); Timothy R. Fitch, Syracuse, NY (US); Melvin D. McCall, Homer, NY (US); Garrison Gomez, Marietta, NY (US); Mark A. McClaude, Syracuse, NY (US); Andrew Longacre, Skaneateles, NY (US); Eunice Sonneville, Ontario, NY (US)

(73) Assignee: Hand Held Products, Inc., Fort Mill, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/729,160

(22) Filed: Dec. 28, 2012

(65) Prior Publication Data

US 2013/0208268 A1    Aug. 15, 2013

Related U.S. Application Data

(60) Continuation of application No. 13/213,905, filed on Aug. 19, 2011, now Pat. No. 8,342,408, which is a division of application No. 12/577,557, filed on Oct. 12, 2009, now Pat. No. 8,002,187, which is a division of application No. 11/804,990, filed on May 21, 2007, now Pat. No. 7,600,687, which is a continuation of application No. 10/982,393, filed on Nov. 5, 2004, now Pat. No. 7,219,841.

(51) Int. Cl.
*G06K 7/10*    (2006.01)

(52) U.S. Cl.
USPC ..................................... 235/462.25

(58) Field of Classification Search
USPC ................ 235/454, 462.01, 462.08, 462.11, 235/462.12, 462.25, 462.31, 462.46, 235/472.01-472.03
See application file for complete search history.

(56) References Cited

U.S. PATENT DOCUMENTS

| | | | |
|---|---|---|---|
| 4,488,679 A | 12/1984 | Bockholt et al. | |
| 4,699,531 A | 10/1987 | Ulinski, Sr. et al. | |

(Continued)

FOREIGN PATENT DOCUMENTS

| | | |
|---|---|---|
| EP | 1357505 A1 | 10/2003 |
| JP | 896062 A | 4/1996 |
| WO | WO 9714110 A1 | 4/1997 |

OTHER PUBLICATIONS

Alan V. Oppenheim, Alan S. Willsky with Ian T. Young, Signals and Systems, Prentice-Hall Signal Processing Series, 1983, pp. 521-526.

(Continued)

*Primary Examiner* — Seung Lee
(74) *Attorney, Agent, or Firm* — Additon, Higgins, Pendelton & Ashe, P.A.

(57) ABSTRACT

A device for processing image data relating to bar codes is described. In one embodiment a bar code verification device is provided having an ergonomic form factor characterized by a domed hand held trigger and a viewing window. The verification device may be disposed in a network that includes a host processor system and other bar code reading devices which may include other bar code verification devices. Processing circuitry for processing image signals corresponding to printed bar codes may be partially disposed within the hand held verification device and partially disposed within a host processor system spaced apart from and associated with the hand held verification device. The hand held verification device may be in wireless communication with the host processor system to which it is associated. The bar code verification system may include signal enhancement modules which interpolate constructed pixel values from actual pixel values and which correct for signal degradation resulting from high frequency spatial sampling.

8 Claims, 25 Drawing Sheets

(56) References Cited

U.S. PATENT DOCUMENTS

| | | |
|---|---|---|
| 4,705,939 A | 11/1987 | Ulinski, Sr. |
| 4,860,226 A | 8/1989 | Martin et al. |
| 5,051,567 A | 9/1991 | Tedesco |
| 5,134,272 A | 7/1992 | Tsuchiya et al. |
| 5,194,720 A | 3/1993 | Reinnagel et al. |
| 5,218,190 A | 6/1993 | Hardesty et al. |
| 5,231,293 A | 7/1993 | Longacre, Jr. |
| 5,285,056 A | 2/1994 | Tedesco et al. |
| 5,313,373 A | 5/1994 | Bjorner et al. |
| 5,334,825 A | 8/1994 | Maddox |
| 5,371,348 A | 12/1994 | Kumar et al. |
| 5,504,315 A | 4/1996 | Hardesty et al. |
| 5,521,370 A | 5/1996 | Hanson |
| 5,564,841 A | 10/1996 | Austin et al. |
| 5,567,934 A | 10/1996 | Zheng et al. |
| 5,569,899 A | 10/1996 | Tedesco |
| 5,569,902 A | 10/1996 | Wood et al. |
| 5,585,616 A | 12/1996 | Roxby et al. |
| 5,600,116 A | 2/1997 | Seo et al. |
| 5,633,488 A | 5/1997 | Spitz |
| 5,729,001 A | 3/1998 | Spitz |
| 5,739,520 A | 4/1998 | Atsumi et al. |
| 5,773,806 A | 6/1998 | Longacre, Jr. |
| 5,773,810 A | 6/1998 | Hussey et al. |
| 5,786,586 A | 7/1998 | Pidhirny et al. |
| 5,837,983 A | 11/1998 | Actis et al. |
| 5,850,080 A | 12/1998 | Herzig et al. |
| 5,914,474 A | 6/1999 | Spitz |
| 5,932,862 A | 8/1999 | Hussey et al. |
| 5,939,697 A | 8/1999 | Spitz |
| 5,942,741 A | 8/1999 | Longacre, Jr. et al. |
| 5,949,052 A | 9/1999 | Longacre, Jr. et al. |
| 5,959,282 A | 9/1999 | Tabuchi et al. |
| 5,979,763 A | 11/1999 | Wang et al. |
| 6,000,615 A | 12/1999 | Spitz |
| 6,000,616 A | 12/1999 | Spitz |
| 6,006,100 A | 12/1999 | Koenck et al. |
| 6,016,135 A | 1/2000 | Biss et al. |
| 6,036,091 A | 3/2000 | Spitz |
| 6,036,094 A | 3/2000 | Goldman et al. |
| 6,036,095 A | 3/2000 | Seo |
| 6,045,047 A | 4/2000 | Pidhirny et al. |
| 6,216,951 B1 | 4/2001 | Swift et al. |
| 6,244,764 B1 | 6/2001 | Lei et al. |
| 6,247,645 B1 | 6/2001 | Harris et al. |
| 6,264,105 B1 | 7/2001 | Longacre, Jr. et al. |
| 6,298,175 B1 | 10/2001 | Longacre, Jr. et al. |
| 6,325,288 B1 | 12/2001 | Spitz |
| 6,328,213 B1 | 12/2001 | He et al. |
| 6,354,503 B1 | 3/2002 | Chiu |
| 6,424,830 B1 | 7/2002 | O'Hagan et al. |
| 6,497,368 B1 | 12/2002 | Friend et al. |
| 6,513,715 B2 | 2/2003 | Heske, III |
| 6,533,175 B1 | 3/2003 | Herzig et al. |
| 6,535,299 B1 | 3/2003 | Scherz |
| 6,561,612 B2 | 5/2003 | Minckler |
| 6,575,367 B1 | 6/2003 | Longacre, Jr. |
| 6,606,395 B1 | 8/2003 | Rasmussen et al. |
| 6,655,595 B1 | 12/2003 | Longacre, Jr. et al. |
| 6,675,203 B1 | 1/2004 | Herrod et al. |
| 6,700,997 B1 | 3/2004 | Spitz |
| 6,739,513 B1 | 5/2004 | McClellan et al. |
| 6,783,071 B2 | 8/2004 | Levine et al. |
| 6,788,293 B1 | 9/2004 | Silverbrook et al. |
| 6,802,449 B2 | 10/2004 | Schuessler |
| 6,814,290 B2 | 11/2004 | Longacre |
| 7,059,525 B2 | 6/2006 | Longacre et al. |
| 7,086,596 B2 | 8/2006 | Meier et al. |
| 7,219,841 B2 | 5/2007 | Biss et al. |
| 7,600,687 B2 | 10/2009 | Biss et al. |
| 8,002,187 B2 | 8/2011 | Biss et al. |
| 2002/0017567 A1 | 2/2002 | Connolly et al. |
| 2002/0023958 A1 | 2/2002 | He et al. |
| 2003/0102376 A1 | 6/2003 | Meier et al. |
| 2003/0197063 A1 | 10/2003 | Longacre |
| 2004/0016812 A1 | 1/2004 | Schmidt et al. |
| 2004/0129784 A1 | 7/2004 | Iwaguchi et al. |
| 2004/0155110 A1 | 8/2004 | Ehrhart et al. |
| 2004/0251307 A1 | 12/2004 | Schmidt et al. |
| 2005/0001035 A1 | 1/2005 | Hawley et al. |
| 2005/0056699 A1 | 3/2005 | Meier et al. |
| 2005/0082371 A1 | 4/2005 | Schmidt et al. |
| 2005/0145698 A1 | 7/2005 | Havens et al. |
| 2005/0199727 A1 | 9/2005 | Schmidt et al. |
| 2005/0199728 A1 | 9/2005 | Schmidt et al. |
| 2006/0169782 A1 | 8/2006 | Schmidt et al. |
| 2010/0084471 A1 | 4/2010 | Biss et al. |

OTHER PUBLICATIONS

Declaration by Applicants' Representative, Sep. 22, 2006. (2 pgs).
International Standard ISO/IEC 15415, First Edition Jun. 15, 2004, Information technology—Automatic identification and data capture techniques—Bar code print quality test specification—Two-dimensional symbols (Reference No. ISO/IEC 15415:2004(E)), pp. i-vi, 1-49.
International Standard ISO/IEC 15416, First Edition Aug. 15, 2000, Information technology—Automatic identification and data capture techniques—Bar code print quality test specification—Linear symbols (Reference No. ISO/IEC 15416:2000(E)), pp. i-v, 1-34.
International Standard ISO/IEC 15416, First Edition Jul. 15,2000, Information technology—Automatic identification and data capture technologies—Bar code verifier conformance specifications—Part 1: Linear symbols (Reference No. ISO/IEC 15426-1:2000(E)), pp. i-v, 1-8.
PCT Notification of Transmittal of the International Search Report and the Written Opinion of the International Searching Authority, International Application No. PCT/US2005/040287, Mar. 10, 2006, 14 pgs.
Skan-A-Matic Corp., The EAN/UPC Verifier to Evaluate and Measure EAN and UPC Code Symbols, Specification Information (4pgs.). Reference published more than one year prior to filed of present application. Reference believed to be published prior to Jul. 18, 1981.

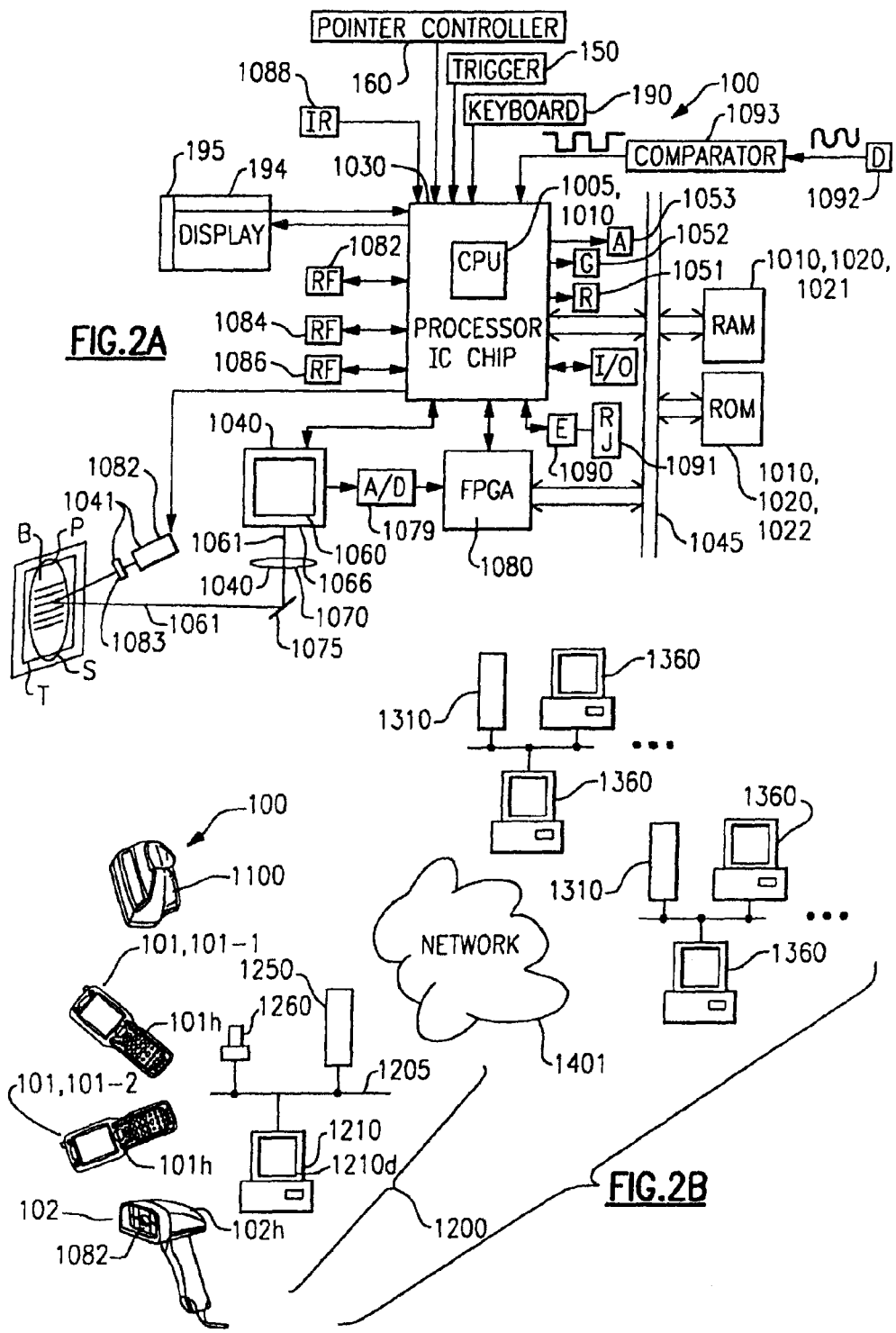

SINC FUNCTION

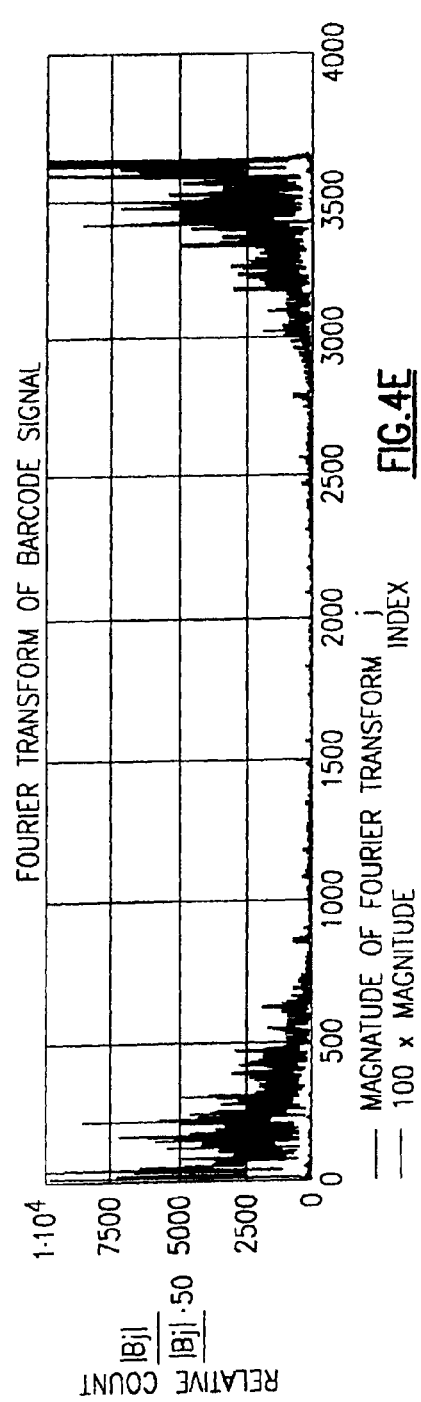
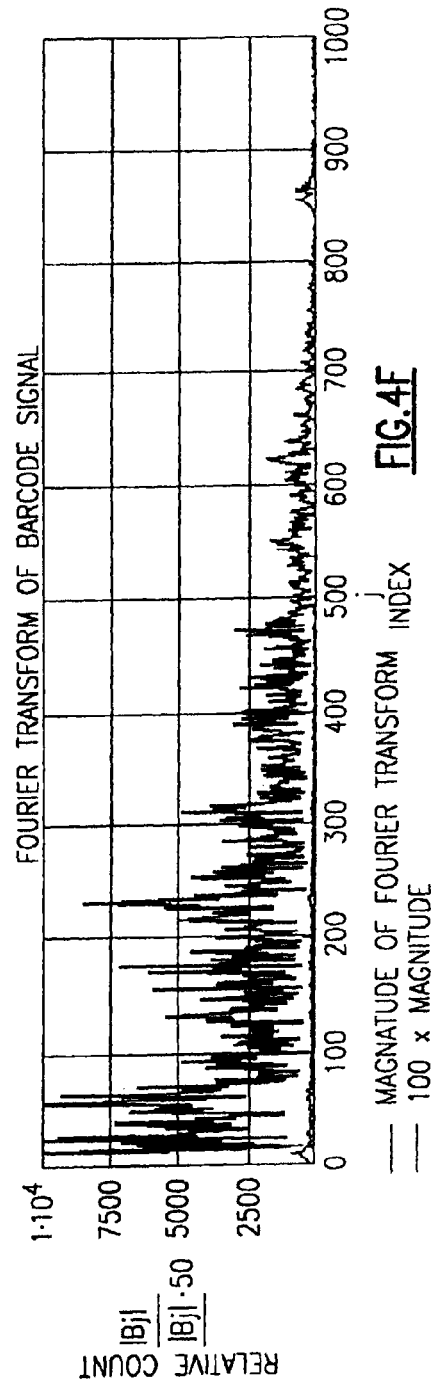
FIG.4E
FIG.4F

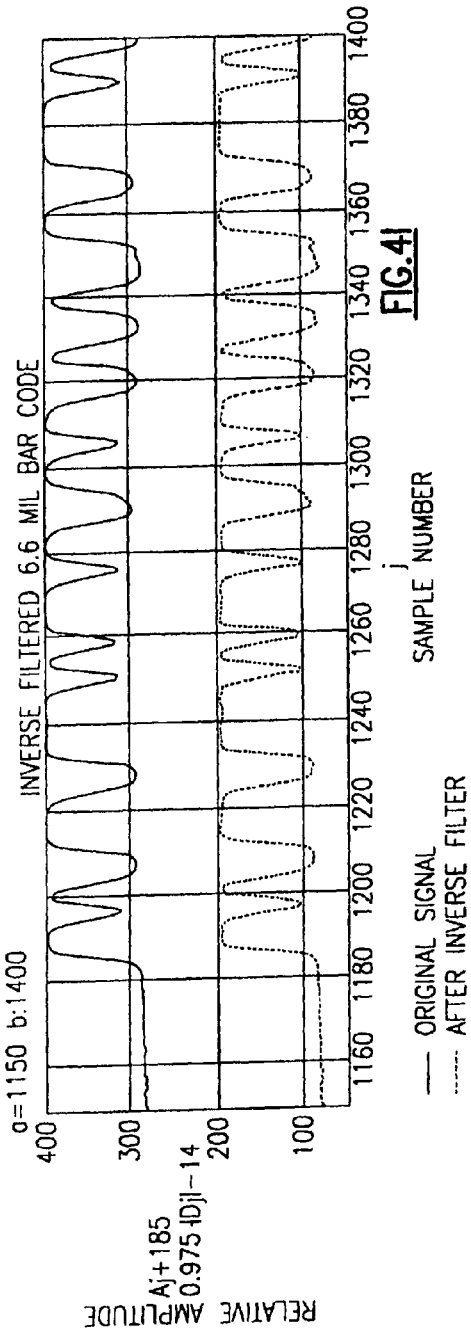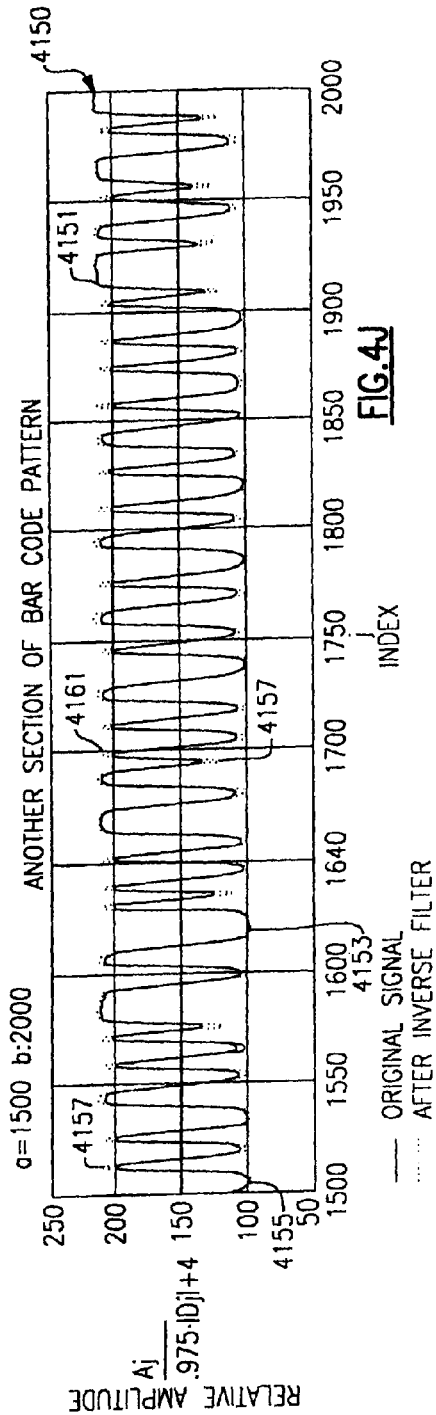

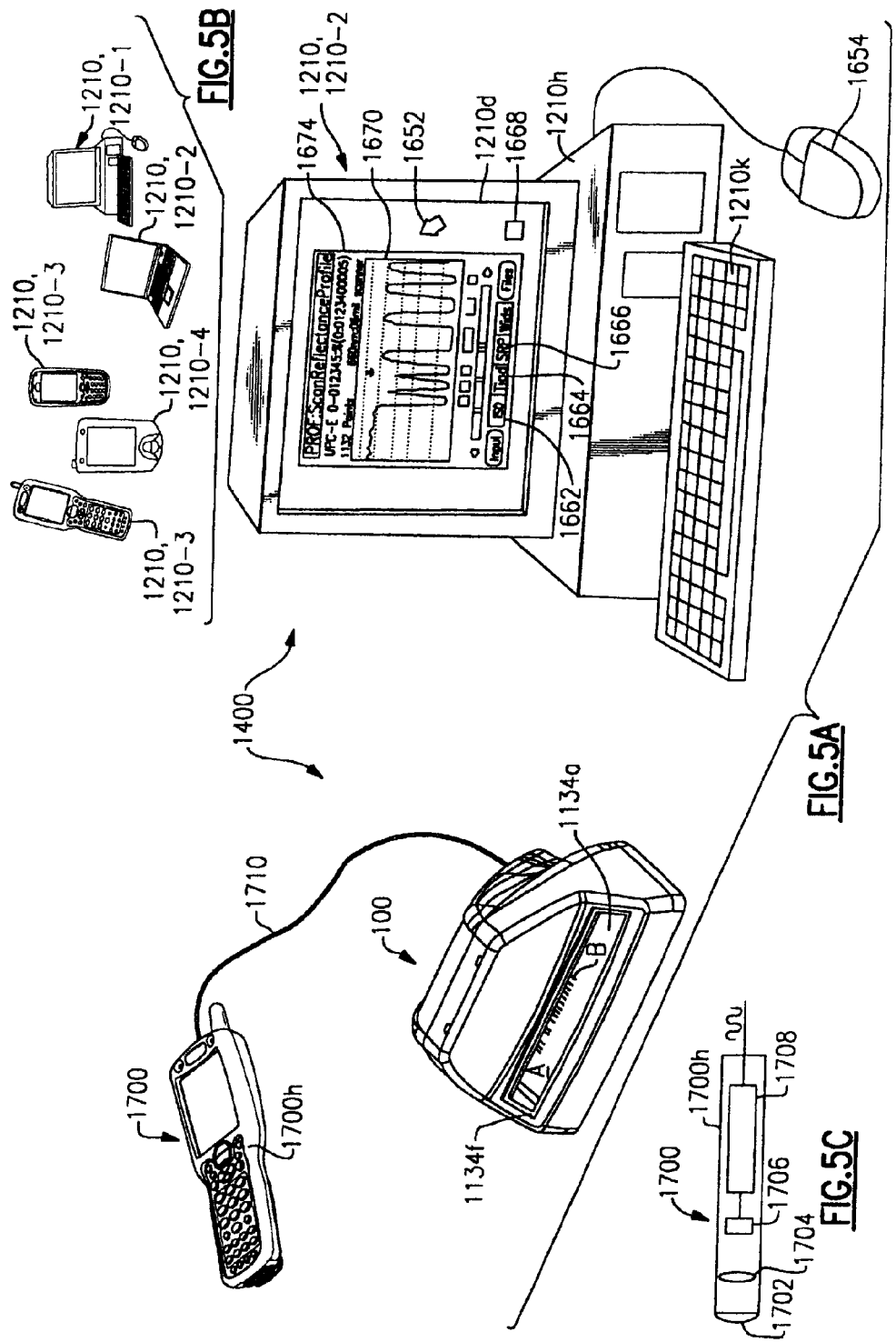

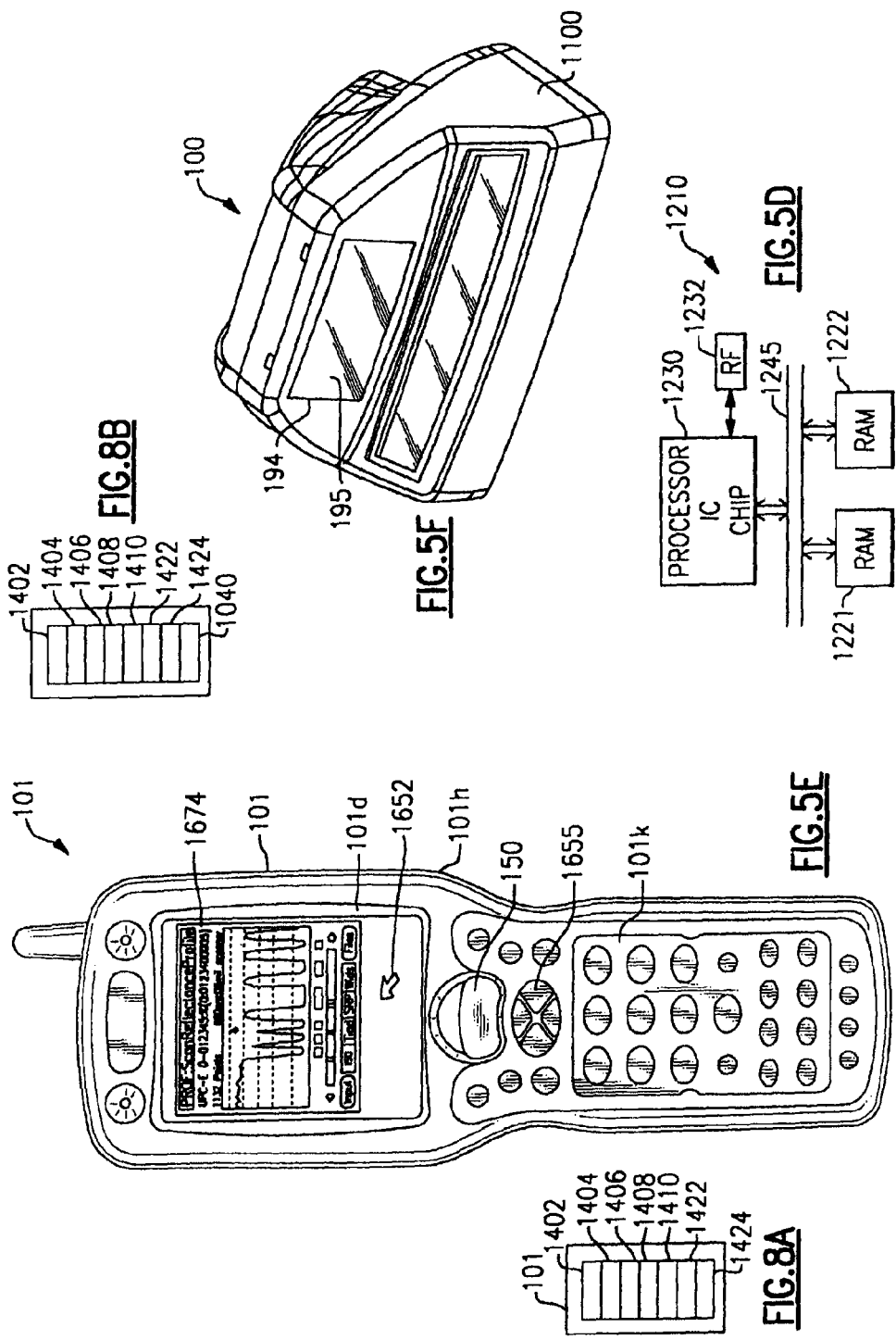

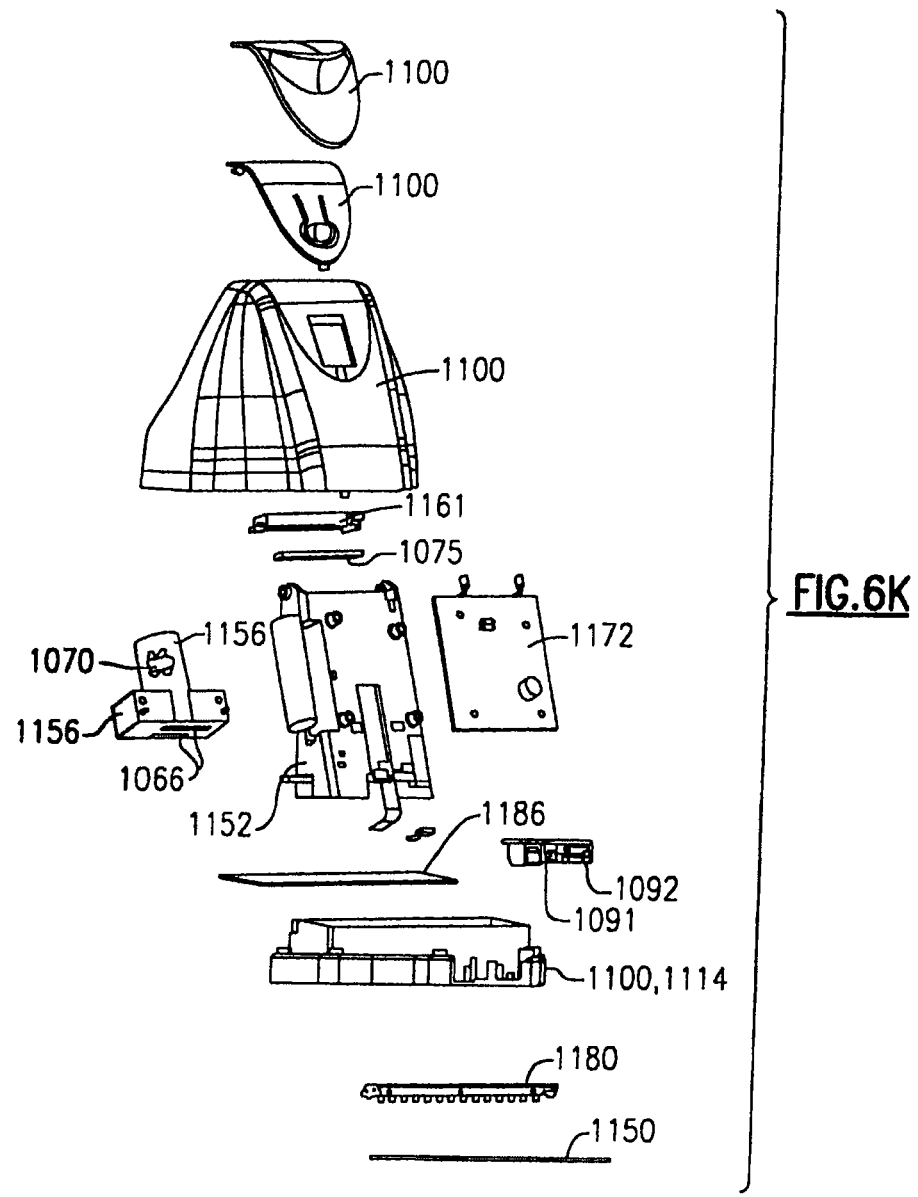

DEVICE AND SYSTEM FOR PROCESSING IMAGE DATA REPRESENTING BAR CODES

CROSS REFERENCE TO RELATED APPLICATIONS

This application is a continuation of U.S. patent application Ser. No. 13/213,905 filed Aug. 19, 2011 entitled "Device and System for Processing Image Data Representing Bar Codes," which is a divisional of U.S. patent application Ser. No. 12/577,557 filed Oct. 12, 2009, now U.S. Pat. No. 8,002,187 entitled "Device and System For Processing Image Data Representing Bar Codes," which is a divisional application of U.S. patent application Ser. No. 11/804,990 filed May 21, 2007, (now U.S. Pat. No. 7,600,687) entitled "Device And System For Processing Image Data Representing Bar Codes," which is a continuation of U.S. patent application Ser. No. 10/982,393, filed Nov. 5, 2004 (now U.S. Pat. No. 7,219,841) entitled, "Device And System For Verifying Quality of Bar Codes." Priority to the above applications is claimed and each of the above applications is incorporated herein by reference in its entirety.

FIELD OF THE INVENTION

The invention relates generally to registers in general and particularly to optical readers.

BACKGROUND OF THE INVENTION

Bar codes are available in a variety of symbologies. One dimensional symbologies include Code 128, Code 39, Interleaved 2 of 5, Codabar, Code 93, Code 11, and MSI. Stacked 1 symbologies include PDF, Code 16K and Code 49. 2D symbologies include Aztec, Datamatrix, and Qcode. Perhaps the most omnipresent bar code symbology is the 1D symbology known as UPC/EAN. UPC/EAN bar codes are standardly used to mark retail products throughout North America, Europe and several other countries throughout the worlds.

Numerous factors can lead to a bar code being unreadable. A bar code symbol can become degraded from extended use, for example, if a wand or other contact reader is swiped across a bar code numerous times. Dust or debris collecting on a bar code, as in a factory or other industrial setting can also negatively affect the capacity of a bar code symbol to be decoded by a reader. The most prevalent forms of degradation actually occur during the printing process, for example ink smearing, improper encodation of the required information, use of improper ink resulting in insufficient bar to space contrast and improperly dimensioned photographic masters. The type of bar code reader being used to read a symbol also has an impact on readability. High quality bar code readers having improved processing functionality and/or improved hardware are able to decode bar code symbols that other bar code readers cannot. Another factor affecting a bar code symbol=s capacity to be decoded is the print quality of the bar code symbol. Bar codes that are printed in accordance with high quality standards can withstand degradation such as caused by use or debris accumulation, and can be read by a variety of bar code readers from high to low quality.

Because bar code print quality has an enormous impact on the capacity of a bar code symbol to be successfully decoded, it is advantageous for users of bar codes such as bar code symbol provides, retail product manufacturers, suppliers, shippers, merchants, and hospitals to monitor the quality of printed bar codes prior to a marked article being circulated for sale or use. The America National Standards Institute (ANSI) Specification ABar Code Print Quality Guideline@ X3.182-1990 established guidelines for verifying bar code symbol print quality. Standards for verifying bar code symbol print quality are also provided in standards promulgated jointly by the International Standards Organization (ISO) and the International Electrotechnical Commission ("IEC"); namely Standard ISO/IEC 15416, "Automatic identification and data capture techniques—Bar code print quality test specification—Linear symbols," a bar code print quality test specification for linear symbols, and ISO/IEC 15415, "Automatic identification and data capture techniques—Bar code print quality test specification—Two dimensional symbols" establishes guidelines for verifying 2D bar code symbol print quality, a bar code print quality specification for two dimensional symbols. According to the above referenced Standards, bar code symbols may be subject to several quality measurements and may be allocated a numerical or letter grade ranging from zero (F) to 4.0 (A). A higher grade means that the bar code is more likely to be successfully decoded, whereas a lower grade means that the bar code is less likely to be successfully decoded. Historically, the AQuality Specification for the UPC Printed Symbol,@ published by the Uniform Code Council, Inc. of Dayton Ohio, established guidelines for evaluating UPC Codes.

While standards have been developed for evaluating bar code symbols, the devices available for conducting such evaluations continue to exhibit limitations. For example, some available bar code verification devices are large, bulky and expensive. Others require significant set up and/or calibration operations prior to use. Still other available verification devices have been noted to be difficult to operate.

There is a need for a bar code verification device and system which is convenient to operate, and which overcomes various noted problems with prior art verification devices.

DESCRIPTION OF THE DRAWINGS

FIG. 2A is an electro-optical block diagram of a hand held verification device according to the invention in one embodiment;

FIG. 2B is an electrical block diagram of a system network including a hand held verification device and a plurality of host processors including a local host processor and several remote host processor;

FIGS. 4C-4K are a series of waveform diagrams and illustrating operation of a verification device according to the invention while executing a high spatial frequency error correction module;

FIG. 5A is a physical form view of a verification system including a hand held verification device interacting with a host processor assembly provided in the specific example by a local area network personal computer;

FIG. 5B shows alternative embodiments of devices which may be employed as a host processor assembly according to the invention;

FIG. 5C is an electro-optical block diagram illustrating an embodiment of an auxiliary reader which may be utilized with a hand held verification device according to the invention;

FIG. 5D is a block diagram corresponding to a host processor assembly according to the invention in one embodiment;

FIG. 5E is an embodiment of the invention wherein a verification system is incorporated in a hand held portable data terminal;

FIG. 5F is an embodiment to the invention wherein a verification system is incorporated into a hand held housing that is especially adapted for use in carrying out print quality measurements;

FIG. 6K is an exploded assembly view of a verification device according to the invention illustrating assembly thereof;

FIGS. 8A-8C are integration diagrams illustrating various processing module integration schemes according to the invention;

DETAILED DESCRIPTION OF THE INVENTION

Figure 1A:
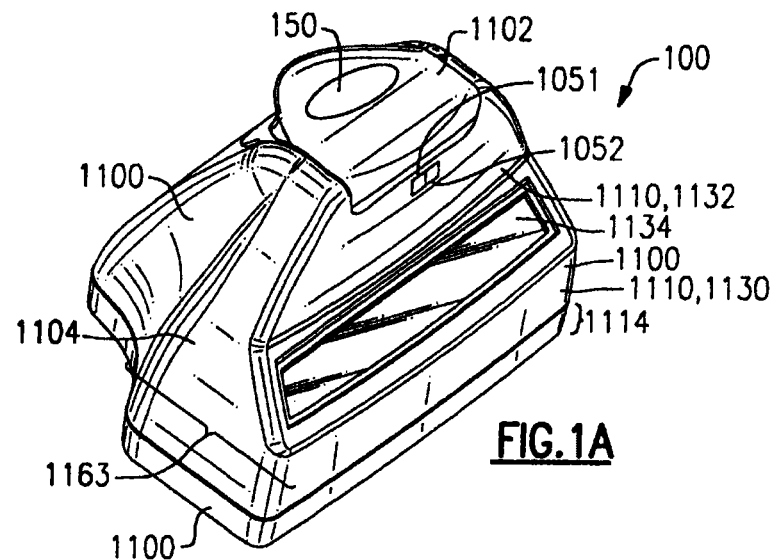
FIGS. 1A-1B are various perspective views of a hand held bar code symbol verification device according to the invention.
Figure 1B:
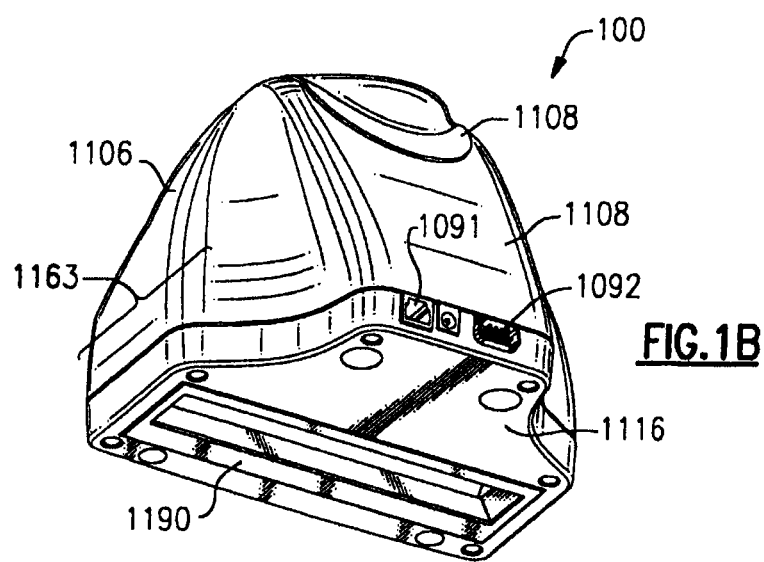
Figure 1C:
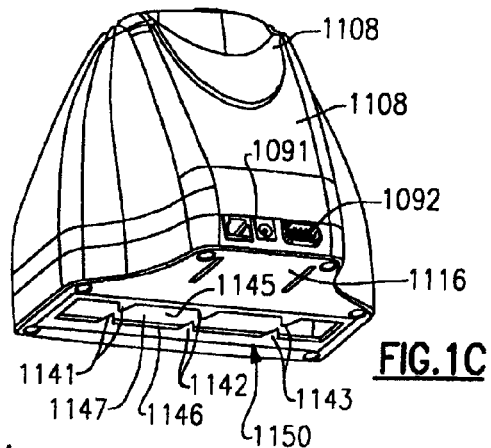
FIG. 1C is a perspective view of a verification device having an alignment member of a different style relative to the device depicted in FIG. 1B.

Perspective views of a bar code verification device 100 according to the invention are shown in FIGS. 1A-1C. Device 100 is configured to be hand held and includes a generally domed shaped housing 1100 having an upper surface 1102 a first side surface 1104 and a second side surface 1106, a front surface 1110 and rear surface 1108. The diameter of housing 1100 generally decreases from bottom to top. Upper surface 1102, side surfaces 1104 front surface 1110 and rear surface 1108 define upper, side, and rear surfaces of device 100 as shown in FIGS. 1A-1C. Referring to further aspects of housing 1100, housing 1100 includes a base portion 1114, which as will be described herein supports an internal support frame 1152 (FIG. 6B) of bar code verification device 100. Base portion 1114 includes a bottom surface 1116 (FIG. 1C) which defines a bottom surface of device 100.

Housing 1100 especially adapts device 100 to carryout measurements on bar codes in that housing 1100 shields ambient light which may be provided, e.g. by sunlight or overhead light. Bar codes that are measured and decoded by device 100 are illuminated by LEDs 1082 or other light sources within housing 1100. By shielding ambient light, housing 1100 assures that consistent illumination conditions are present between measurement and decode sessions of device 100. Device 100 is configured so that base 1114 is supported on a horizontal surface (e.g., a table top) when device 100 is used to decode a measure print quality of bar codes. More specifically, in use, a substrate, s, such as a sheet of paper carrying a bar code to be subject to decoding and print quality measuring is first placed on a horizontal surface. Device 100 is then moved by an operator into such position relative to the substrate, s, that housing 1100 covers the bar code symbol, B. Specifically, when device 100 is positioned to measure print quality and to decode bar codes opening 1141 (which in the embodiment of FIGS. 6E-6J is defined by a transparent window) of base surface 1116 is position over the bar code.

Device 100 further includes a trigger 150. Trigger 150 in the embodiment of FIGS. 1A-1C is disposed on a top surface of device 100. Trigger 150 could also be disposed on another surface of device 100, such as a front surface or rear surface of device 100. Trigger 150 could also be disposed partially on a pair of adjoining surfaces of housing 1100. Further, more than one trigger 150 may be disposed on device 100.

Referring to further aspects of device 100, the front surface 1110 of housing 1100 includes outer portion 1130 and stepped-in inner portion 1132. Disposed between outer portion 1130 and inner portion 1132 is window 1134. Window 1134 could be of a transparent material, thereby preventing foreign objects from entering the inside of the housing. It may be advantageous to have window 1134 include a light attenuating material that will reduce the level of ambient light entering housing 1100, thereby reducing the false lighting that might otherwise be incident on the bar code under test. The light transmissivity of window 1134 will be properly selected to reduce this interference to acceptable levels. For example neutral density filters, such as the Kodak Wratten filters, might be used. Window 1134 in one embodiment exhibits a transmissivity of about 1%. There may be other conditions where colored filters might be used, or in some cases combinations of neutral density and color filters might be used. Other filters might be used to attenuate specific spectral components, such IR stop filters. Window 1134 is disposed at and angle so that window 1134 is angled upward from outer portion 1130 to inner portion 1132. Window 1134 could also be disposed substantially horizontally with respect to a horizontal plane. Window 1134 allows bar codes printed on a substrate, s, (such as a sheet of paper) to be viewed while device 100 is used to measure print quality of a bar code symbol. It will be seen that housing 1100 and window 1134 may be configured so that window 1134 is removably received thereon. In the view of FIG. 5B (showing device with window 1134 removed), it is seen that window frame 1134f defining window aperture 1134a can be configured to replaceably receive window 1134. Specifically, frame 1134f and window 1134 can be sized so that window 1134 rests within frame 1135 and is further stabilized by the force of gravity. In use, window 1134 might be manually removed from frame 1134f during alignment of device 100 relative to bar code, B, then, after alignment is achieved, placed back into frame 1134f prior to a trigger signal being actuated. Window 1134 may be made opaque to further discourage ambient light rays from reaching bar code, B.

For facilitating the centering of a field of view of device 100 on a bar code subject to measuring bottom surface 1116 of device 100 includes an alignment member 1150 comprising alignment formations 1140, 1141, 1142. Alignment formations 1141, 1142, and 1143 can be viewed through window 1134. In use, a user centers device 100 on a bar code symbol such that center alignment formations 1142 are located approximately at a horizontal center of a bar code while outer alignment formations 1141, 1143 are located approximately at edges of a bar code. Forward edge 1146 and rear edge 1145 of opening 1147 are spaced apart such that the spacing between forward straight edge 1146 and rear straight edge 1145 aids in the vertical alignment of device 100 with respect to a bar code symbol to be subject to print quality measurement, also known as symbol verification. In the embodiment shown, forward and rear edges 1146 and 1145 have a spacing of about 0.5 inches. As such, the spacing allows a user to readily confirm that device 100 is vertically centered, e.g. by noting similarly sized gaps between a top of a bar code and forward edge 1146 and a bottom of a bar code and rear edge 1145. Additional aspects of alignment member 1150 and alternative embodiments thereof are described in connection with FIGS. 6E-6J.

Figure 1D:
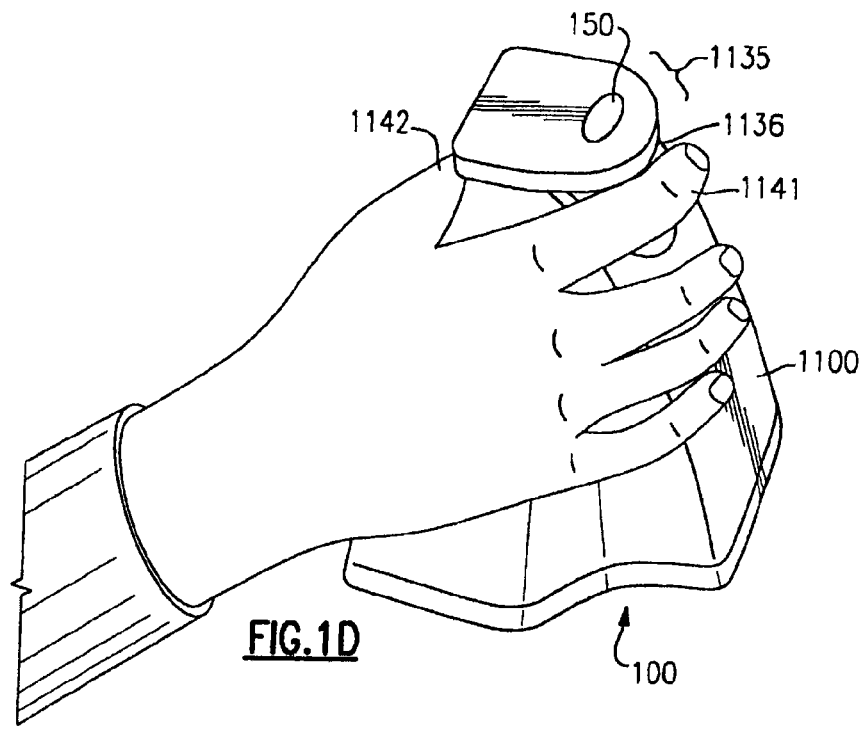
FIG. 1D is a perspective view of a verification device according to the invention being held by an operator, the verification device having an enlarged head portion that aids in the maneuverability of the device.
Figure 1F:
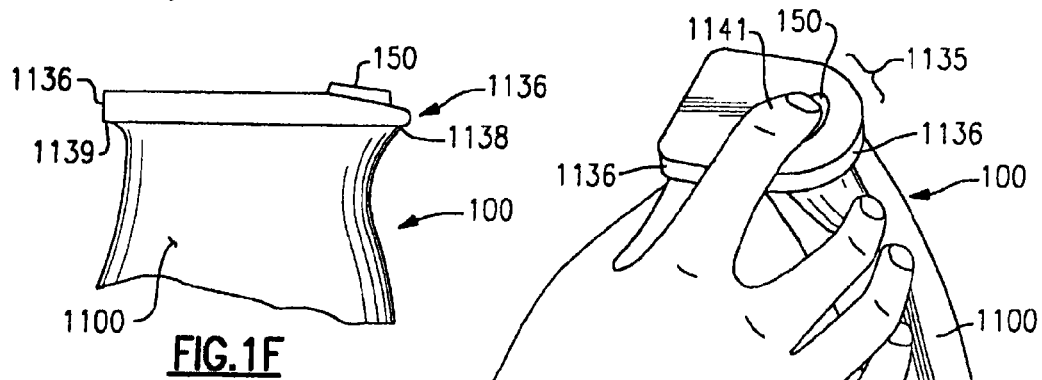
FIG. 1F is a side view of the verification device shown in FIG. 1D.
Figure 1E:
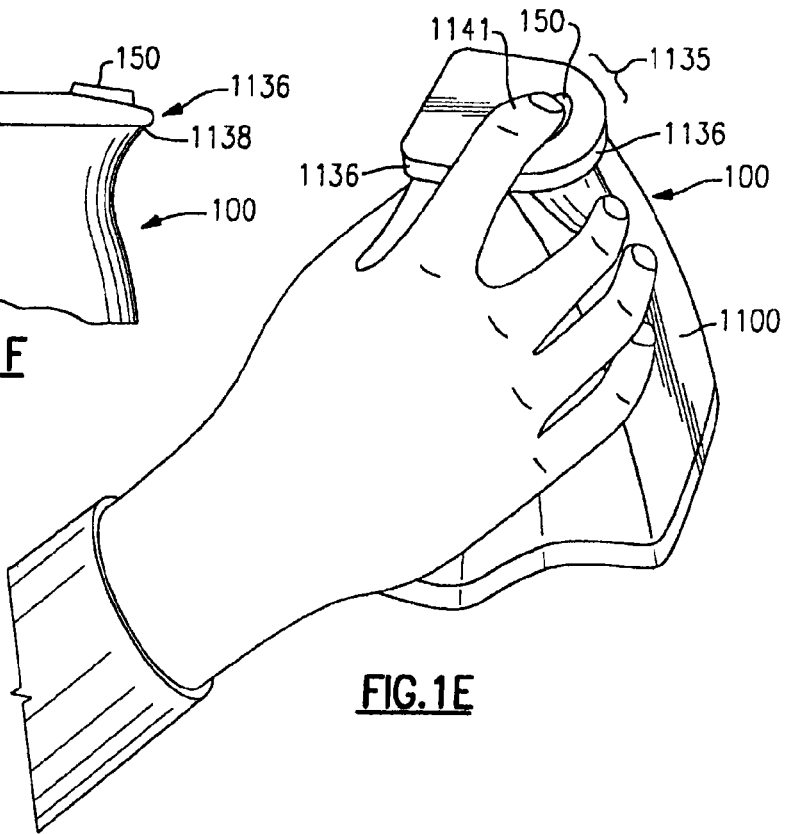
FIG. 1E is another perspective view of the verification device of FIG. 1D, showing an operator actuating a trigger of the device.

Referring to FIGS. 1D-1F, housing 1100 of device 100 in an embodiment of the invention can include a head portion 1135 that defines a lip 1136 extending outwardly from the lateral surfaces (i.e. surfaces 1104, 1108, 1110) of housing 1100. Lip 1136 may be continuously formed about head portion 135 or else may be discontinuous. Lip 1136 may include surface regions such as region 1138 and region 1139 that are configured to engage an operator's finger and/or thumb when an operator lifts device 100 upwardly. As indicated by the side view of FIG. 1F, Lip 1136 may have portions defining finger or thumb engagement surfaces 1138, 1139 at spaced apart positions about the circumference of head 1135. Where engagement surfaces 1138, 1139 are formed at spaced apart positions, a first engagement surface region 1138 may engage a finger 1141 of an operator as illustrated in FIG. 1D, while a second engagement surface region 1139 engages a thumb 1142 of an operator. Enlarged head portion 1135 greatly enhances the ease with which device 100 can be picked up and moved from position to position on a substrate, s. In the embodiment of FIGS. 1D-1E trigger 150 is positioned in a position that is coordinated with the positioning of lip 1136. It is seen that when device 100 is lifted and moved with utilization of engagement surfaces 1138, 1139, and then subsequently rested on a substrate, s, an operator's finger is positioned in such position in close proximity with lip 1136 that it can readily be moved into a trigger actuation position as depicted in FIG. 1E without an operator releasing device 100 from the grasp of the hand including finger 1141. In a further aspect of device 100, housing 1100 defines side grippings formation 1163. Side gripping formations 1163, 1164 are sized to a width such that grippings formations 1163, 1164 are easily grasped by a human hand. Further, the surface of housing 1100 defining gripping formation 1163 is contoured as shown so as to enhance the ease with which gripping formations 1163 may be grasped while reducing the likelihood of an operator's hand slipping while the operator stabilizes device 100 on a substrate. Accordingly, an operator can grip side grasping formation 1163 to stabilize device 100 on a substrate, s, during reading.

Figure 9A:
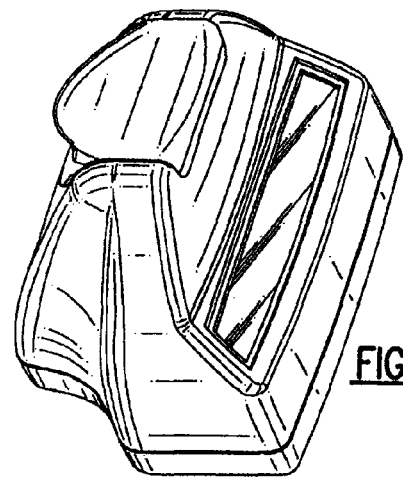
FIG. 9A is a perspective view of a hand held verification device according to the invention.
Figure 9B:
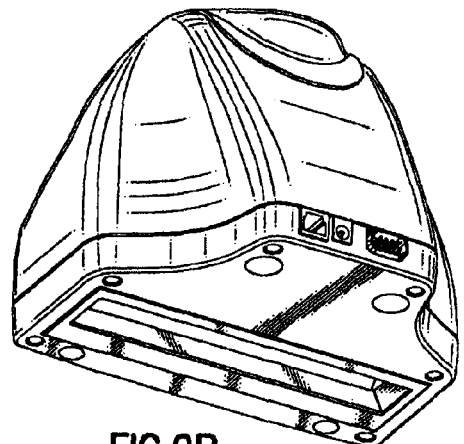
FIG. 9B is another perspective view of the hand held verification device shown in FIG. 9A.
Figure 9C:
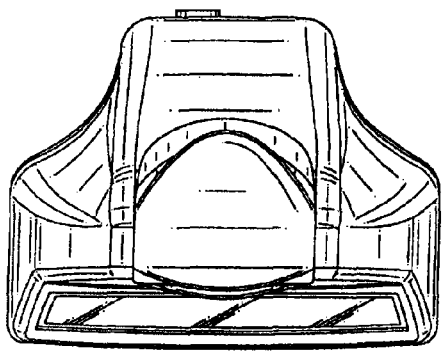
FIG. 9C is a top view of the hand held verification device shown in FIG. 9A.
Figure 9D:
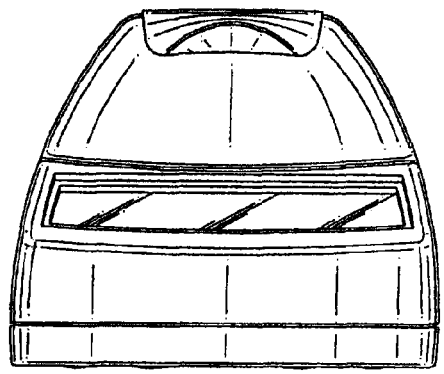
FIG. 9D is a front view of the hand held verification device shown in FIG. 9A.
Figure 9E:
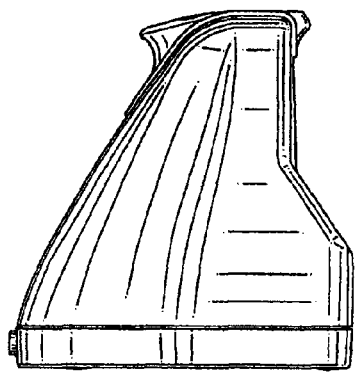
FIG. 9E is a first side view of the hand held verification device shown in FIG. 9A.
Figure 9F:
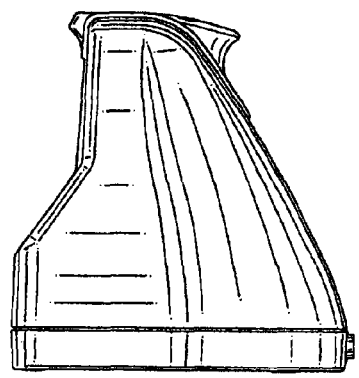
FIG. 9F is a second side view of the hand held verification device shown in FIG. 9A.
Figure 9G:
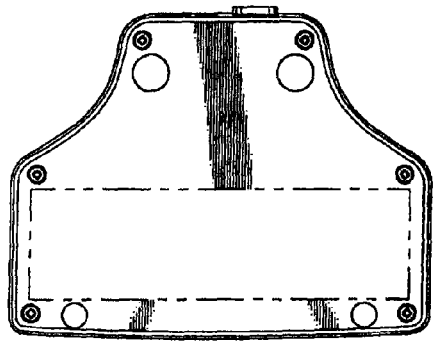
FIG. 9G is a bottom view of the hand held verification device shown in FIG. 9A with alignment member deleted.
Figure 9H:
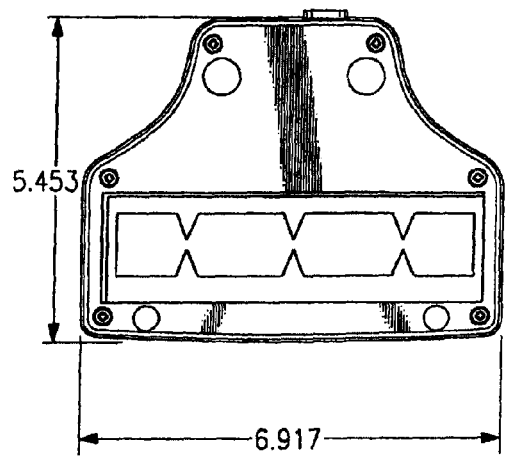
FIG. 9H is another bottom view of the hand held verification device of FIG. 9A with an alignment member shown and dimensional information (in inches) embedded in the drawing.
Figure 9I:
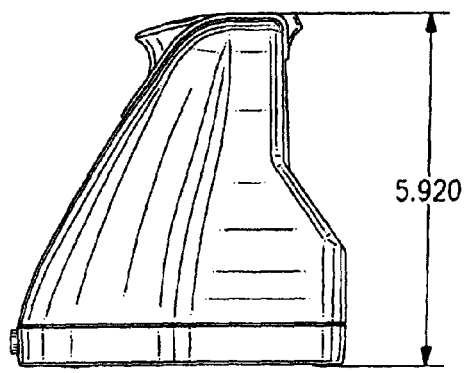
FIG. 9I is a tangent line side view of the bar code verification device shown in FIG. 9A with dimensional information (in inches) embedded in the drawing.

Dimensional information for device 100 is presented in FIGS. 9H and 9I. The embodiment of FIGS. 9A-9G is dimensioned precisely to the dimension of FIGS. 9H and 9I, and the remainder of the embodiments described herein are dimensioned approximately in accordance with the dimensional information provided in FIGS. 9H and 9I. It will be understood that since the depiction of the elements of device 100 are shown in true proportion, the dimensions of any specific feature of device 100 can be determined from the dimensional information presented in FIGS. 9H and 9I although the specific feature dimensions may not be expressly listed. In one specific embodiment of the invention, one or more features of device 100 is scaled by a factor of ±25% relative to the dimensional information of FIGS. 9H and 9I. In another embodiment, one or more features of device 100 is scaled by a factor of ±50%. In another embodiment, one or more features of device 100 is scaled by a factor of ±75% relative to the dimensional information of FIGS. 9H and 9I.

A block electro-optical diagram of device 100 is shown in FIG. 2A. Control circuit 1010 includes a central processing unit (CPU) 1005 and memory 1020. CPU 1005 may be disposed on processor IC chip 1030, while memory 1020 may be incorporated partially in IC chip 130 and partially in a plurality of memory IC chips such as ROM IC chip 1022 and RAM IC chip 1021. EROM IC chip 1022 and RAM IC chip 1021 may be in communication with microprocessor IC chip 1005 via system bus 1045. Shown as being provided on an IC processor chip 1030 in communication with a memory 1020, control circuit 1010 can include in place of or in addition to the elements shown additional types of electrical circuits, e.g. analog circuits, and digital logical circuits including programmable logic circuits.

Figure 6A:
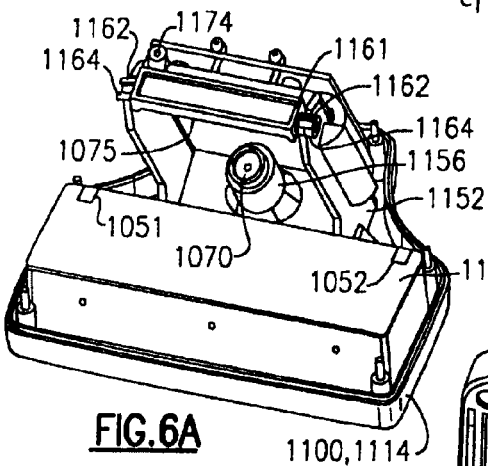
FIGS. 6A-6D are various assembly views of a device according to the invention.
Figure 6B:
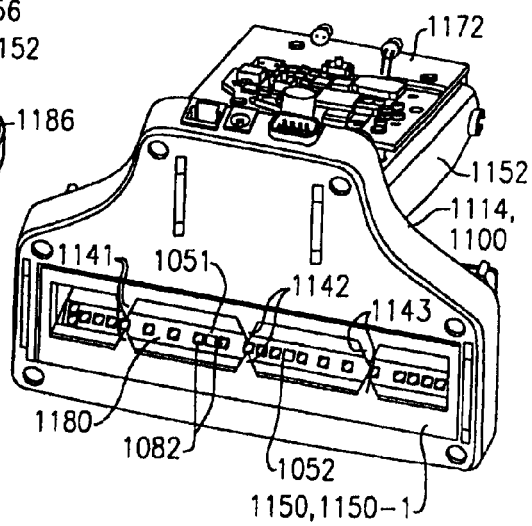
Figure 6C:
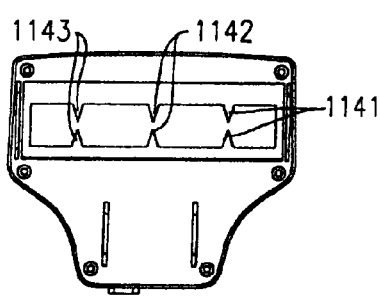
Figure 6D:
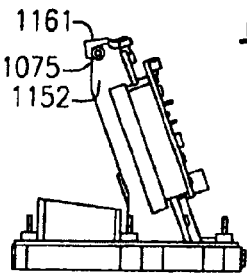

Device 100 also includes an image signal generating system provided by solid state image sensor 1060, available in such technologies as CCD, CMOS, and CID. Solid state image sensor 1060 may be a monochrome or color one-dimensional image sensor or a two-dimensional image sensor. One-dimensional solid state image sensors typically have a single row of photosensitive picture elements or pixels but are available in models having a limited number (e.g., 2) rows of pixels. Two-dimensional solid state image sensors generally have a plurality of photosensitive picture elements or pixels which are formed in a pattern including a plurality of rows and a plurality of columns of pixels. Device 100 further includes an imaging optics 1070 focusing an image onto an active surface of image sensor 1060 and reflector 1075. Device 100 includes a folded imaging axis 1061 folded by reflector 1075. Imaging optics 1070 may focus an image of a barcode, B, disposed on a substrate, s, onto image sensor 1060. The substrate, s, may be e.g. a piece of paper or a film. Target, T, of substrate, s, is the region of substrate, s, corresponding to the field of view of device 100. Image sensor 1060 may be incorporated on an image sensor IC chip 1066 having disposed thereon image sensor control circuitry, image signal conditioning circuitry, and an analog-to-digital converter. A/D converter 1079 may also be separate from IC chip 1066. Device 100 may further include a field programmable gate array 1080 ("FPGA") or the functionality of FPGA 1080 may be incorporated onto processor IC chip 1030. Operating under the control of control circuit 1010, FPGA 1080 manages the capture of image data into RAM 1021. Device 100 further comprises output indicators including red LEDs 1051, green LEDs 1052 and acoustic output device 1053. Physical form views of LEDs 1051, 1052 are shown in FIGS. 1A, 6A and 6C. It is seen that device 100 can have redundant indicators 1051, 1052.

A parts list for circuit elements as shown in FIG. 2A, in one embodiment, is presented in Table I, herein below.

TABLE 1

| Circuit Element | Part |
| --- | --- |
| Processor IC Chip 1030 | Motorola DRAGONBALL MC9328MXL (150 MHZ) |
| Image Sensor Chip 1060 | Toshiba TCD 1305P |
| Radio 1086 | EYSF2CAXX |
| A/D 1079 | National ADC1173 (8 Bit) |

Another embodiment is summarized in Table 2 below.

TABLE 2

| Processor IC Chip 1030 | Motorola DRAGONBALL MC9328MXL (150 MHZ) |
| --- | --- |
| Image Sensor Chip 1060 | ICMEDIA, ICM105ATU |
| Radio 1066 | EYSF2CAXX |

The circuit of FIG. 2A and the optical elements describe relative thereto may be provided on an OEM image engine of the type available from Hand Held Products, Inc. of Skaneateles Falls, N.Y., such as an 1D IT3800E image/engine or a 2D IT4010/80 image engine.

When control circuit 1010 receives a trigger signal, control circuit 1010 automatically sends appropriate control signals to image sensor chip 1066. Image sensor chip 1066 in response thereto automatically exposes photosensitive pixels of image sensor 1060 to light and generates image signals. Also in response to receipt of a trigger signal, control circuit 1010 energizes LEDs 1082, so that substrate, s, is illuminated at least during exposure periods of image sensor 1060. Light from LEDs 1082 may be shaped by optional shaping optics 1083. Illumination assembly 1141 comprising LEDs 1082 and optical shaping optics 1083 project an illumination pattern, P, onto substrate, s. LEDs 1082 may be replaced by one or more other light sources such as incandescent lamps, fluorescent lamps, and lasers. The image signals are thereafter automatically converted into digital values by analog-to-digital converter 1079 or by an onboard analog-to-digital converter of image sensor IC chip 1066. The digital values are received by FPGA 1080 and transferred into RAM 1021. In accordance with bar code decoding and print quality measurement programs stored in ROM 1022, control circuit 1010 attempts to decode a bar code symbol represented in the captured image data performs various measurements to grade the bar code symbol. The capture of image data, decoding, and measurement of print quality by processing of image data occur automatically in response to a trigger signal being received. Control circuit 1010 may be configured to continuously capture image data and process bar code symbols represented therein as long as a trigger signal is received. Device 100 may be configured so that device 100 receives a trigger signal when trigger button 150 is actuated. Device 100 may also be configured to receive a trigger signal when a control button, e.g., button 1668 (FIG. 5A) of a spaced apart device, e.g., of host processor assembly 1210 is actuated.

Imaging assembly 1040, which in the embodiment described thus far includes an image sensor chip 1066 and imaging optics 1070 may be provided in the form described in connection with FIGS. 2A-2C. Imaging assembly 1040 may also be provided by a laser scan engine, such as an SE1000 scan engine of the type available from Symbol Technologies, Inc. of Holtsville, N.Y.

IC chip 130 may include a plurality of serial I/O interfaces such as general purpose I/O, USB, and Ethernet interfaces and a plurality of parallel interfaces such as CompactFlash and PCMCIA.

Device 100 may further include a plurality of communication links such as a first radio frequency communication transceiver 1082, a second radio frequency transceiver 1084, a third radio frequency transceiver 1086, and an IR communication link 1088 facilitating communication between device 100 and an external device spaced apart from device 100. As seen in FIG. 2B, device 100 may be part of a local area network ("LAN") 1200 including a spaced apart and separately housed local host processor assembly 1210 and other portable hand held devices 101-1, 101-2, 102. Gun style hand held device 102 may be provided e.g., by an IT4410 hand held reader, an IT4710 reader, an IT4600 reader, an IT4800 reader or an IT4X80 reader. All of the above readers are manufactured by Hand Held Products, Inc. of Skaneateles Falls, N.Y. LAN 1200 may further include such components as a system backbone 1205, an access point 1260, and a server 1250. As is discussed with reference to FIG. 5D, host processor assembly 1210 may have many components similar to those of device 100. Host processor assembly 1210 may include a processor IC chip 1230, a system RAM 1221, a program memory or system ROM 1222 and a radio frequency transceiver 1282. Transceiver 1282 may be disposed within housing 1210h or may be external e.g., tethered to housing 1210h. By configuring wireless communication between device 100 and host processor assembly 1210 so that a radio frequency transceiver of device 100, e.g. transceiver 1082 and a radio frequency transceiver of host processor assembly, e.g., transceiver 1282 communicate according to the same communication protocol or standard. In a first embodiment, device 100 and host processor assembly 1210 are configured so that transceivers 1082 and 1282 do not transmit signals of above about 3 milliwatts. Configuring device 100 and host processor assembly 1282 so that transceivers 1082 and 1282 transmit power-limited signals of below about 3 milliwatts reduces the likelihood of interference with other electrical equipment which may be in the vicinity of device 100 and host processor assembly 1282. Further in accordance with a first embodiment, device 100 and host processor assembly 1282 are configured so that transceivers 1082 and 1282 conduct spread spectrum frequency hopping data transmissions. Configuring device 100 and host processor assembly 1210 to conduct spread spectrum frequency hopping data transmissions further limits the likelihood of radio interference with other radio transmitting electrical devices in the vicinity of device 100 and host processor assembly 1210. Still further, device 100 and host processor assembly 1210 are configured in accordance with a first embodiment so that when device 100 and host processor assembly 1210 are in communication range of one other, transceiver 1082 and transceiver 1282 automatically communicate with one another to determine whether device 100 is to transmit data to host processor assembly 1210. The first embodiment may be conveniently realized if transceivers 1082, 1282 are Bluetooth transceivers appropriately established in accordance with the Bluetooth data transmissions protocol. According to one embodiment of device 100, radio frequency transceiver 1082 may be a Bluetooth radio frequency transceiver, radio frequency transceiver 1084 may be an 802.11 radio frequency transceiver, while radio frequency transceiver 1086 may be a GSM/GPRS radio frequency transceiver. 802.11 radio frequency transceiver, 1084 generally enables longer range LAN communications than Bluetooth radio frequency transceiver 1082. GSM/GPRS radio transceiver 1086 enables long range cellular data communications.

Devices 101-1 and 101-2 are "PDT" devices having housing 101h, while device 102 has housing 102h. Electrical circuit components and optical components described with reference to FIG. 2A may be incorporated into housing 101h and housing 102h. Devices 100, 101-1, 101-2, 102 are portable such that they are spaced apart from host processor assembly 1210 and may be freely moved by an operator into any desired orientation relative to host processor assembly 1210. In addition to having wireless communication links, device 100 may include various physical connector interfaces such as an RJ45 connector 1091 associated with Ethernet interface 1090 enabling hard wired communication with host processor 1210. Device 100 may further be in communication with a plurality of offsite remote host processors 1310 located several miles to thousands of miles away from device 100. Remote host processors 1310 may be in communication with device 100 via a wide area network 1401, which may be the Internet. Device 100 may include a browser enabling a user of device 100 to view on display 194 (FIG. 5F) a web page stored in one of a remote host processor 1310 and to navigate between websites stored on a variety of host processors 1310. As will be described herein below, device 100 may include connector 1092, such as a "D Connector" enabling connection of an auxiliary reader unit to device 100. Signals input to device 100 by an auxiliary reader unit may be processed by comparator 1093 as will be described in connection with FIG. 5A. Device 100 may communicate directly with network 1400 or indirectly with network 1400 by utilization of network elements of the local area network 1200 including device 100, and local host processor 1210. Housing 1100 may encapsulate and support all of the electrical components and all of the optical components shown in the electro-optical diagram of FIG. 2A.

Figure 2C:
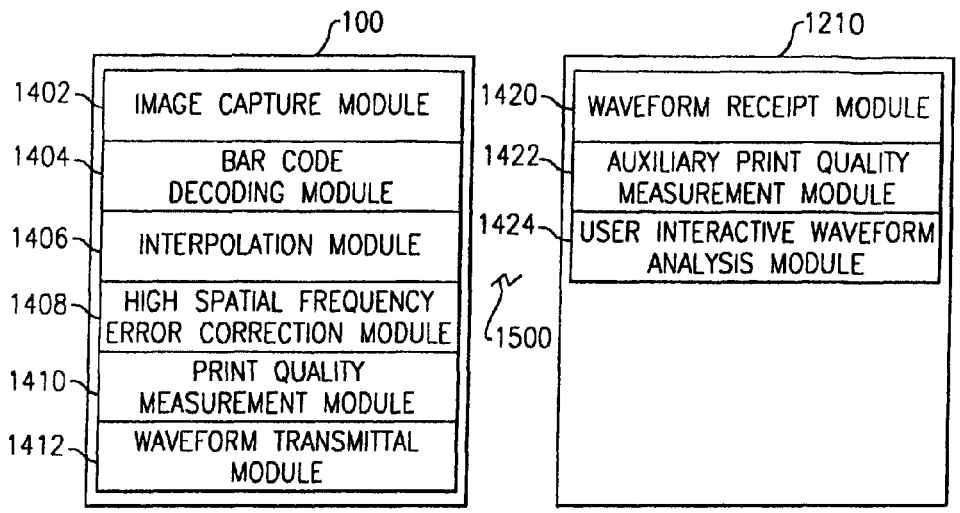
FIG. 2C is a schematic diagram showing the integration of various processing modules of the invention in one embodiment.

As is indicated by the system diagram of FIG. 5A, device 100 containing the electrical and optical components of the diagram of FIG. 2A is in communication with auxiliary reader unit, e.g., unit 1700. From time to time it may be desirable to capture image data for processing by the circuit of FIG. 2A with use of image sensing components other than the components contained within device 100. The system 1400 of FIG. 5A includes an auxiliary wand reader 1700. Wand reader 1700 may have a rugged tip 1702 adapted to contact paper, an imaging lens 1704, a single element photodetector 1706, and signal processing circuitry 1708 developing signals output by sensor 1706 into an analog waveform as wand 1700 is dragged across a bar code. Hand reader 1700 may further have a hand held housing 1700h supporting the above elements. Wand reader 1700 produces image signals when it is physically dragged across a bar code. The image signals produced by wand reader 1700 are smooth waveforms generally regarded to be of higher resolution than those that can be produced by multiple pixel image sensor 1060. System 1400 may be configured so that wand reader 1700 is detachably attachable to the device 100. Specifically, a connector of cable 1710 extending from wand reader 1700 may be detachably attached to connector 1092 of device 100 (see FIGS. 1A, 2A). Device 100 can be configured so that when wand reader 1700 spaced apart from device 100 is connected to device 100, signals output by wand reader 1700 are received and processed by device 100. Specifically, with reference to FIG. 2A, analog signals output by wand reader 1700 are input into comparator 1093. Comparator 1093 subjects the input analog waveform to an adaptive threshold test to produce a digital output signal which is input to processor IC chip 1030. Device 100 then processes the input image signals in accordance with the processing modules described in connection with FIG. 2C.

Device 100 in one embodiment automatically interrogates connector 1092 to determine whether auxiliary reader 1700 has been connected. If device 100 determines that auxiliary reader 1700 has been connected, device 100 automatically waits for image signals to be received from reader 1700, and automatically processes the signals when they are received in accordance with processing modules 1402, 1404, 1408, 1410 and 1412. In one embodiment, auxiliary reader 1700 has substantially the electrical and optical components of FIG. 2A, but has a housing of a different form factor. For example, auxiliary reader 1700 may have a gun style form factor such as reader 102. An alternative form factor might be useful, e.g., for reading bar codes in hard to access locations. Auxiliary reader 1700 may also lack one or more of modules 1408, 1410, 1412.

In use, verification device 100 is interactive with and is used in association with host processor assembly 1210. Host processor assembly 1210 may be provided by e.g. a personal computer as is shown in FIG. 2B. However, it will be understood that host processor assembly 1210 can be provided by any display-equipped device 100 having suitable processing functionality. As shown in FIG. 5B host processor 1210 can be provided by an e.g., a PC 1210-1, a portable laptop computer 1210-2, a hand held portable data terminal 1210-3, 1210-5, or a hand held personal data assistant, PDA 1210-4. Further, any functionality described herein for local host processor assembly 1210 could readily be accomplished with use of a remote host processor assembly such as any one of the devices labeled assembly 1360 shown in FIG. 2B.

As indicated previously, a system 1400 that comprises verification device 100 and host processor assembly 1260 e.g. can have a plurality of processing modules. A breakdown describing the integration of such processing modules in the various components of system 1400 in one embodiment is described with reference to FIG. 2C.

In the schematic diagram of FIG. 2C, verification device 100 includes an image capture module 1402, a bar code decoding module 1404, an interpolation module 1406, a high spatial frequency error correction module 1408, a bar code print quality measurement module 1410, and a waveform transmittal module 1412, whereas host processor assembly 1210 includes a waveform receipt module 1420, user-interactive waveform analysis module 1424 and an auxiliary print quality assessment module 1422. Image capture module 1402 is generally executed by control circuit 1010 in response to trigger 150 being actuated. The execution of modules 1404, 1406, 1408, 1410, 1412, 1420, and 1422 also follow automatically in response to the actuation of trigger subsequent to the execution of image capture module. The execution of image capture module 1402 generally involves the transmittal of commands from control circuit 1010 to image sensor chip 1066 and the processing of an analog waveform produced by image sensor chip 1066 into digital form with use of an A/D converter. The remaining modules 1404, 1406, 1408, 1410, 1412, 1420, 1422, and 1424 are conveniently embodied in software (that is, they are performed with use of processor IC chip 1030 or host processor assembly 1210 in response to a program stored in a memory e.g. memory 1021). However, modules 1404, 1406, 1408, 1410, 1412, 1420, 1422, and 1424 can comprise hardware circuit components and combinations of hardware and software components. Aspects of the various processing modules are described herein below.

Figure 2D:
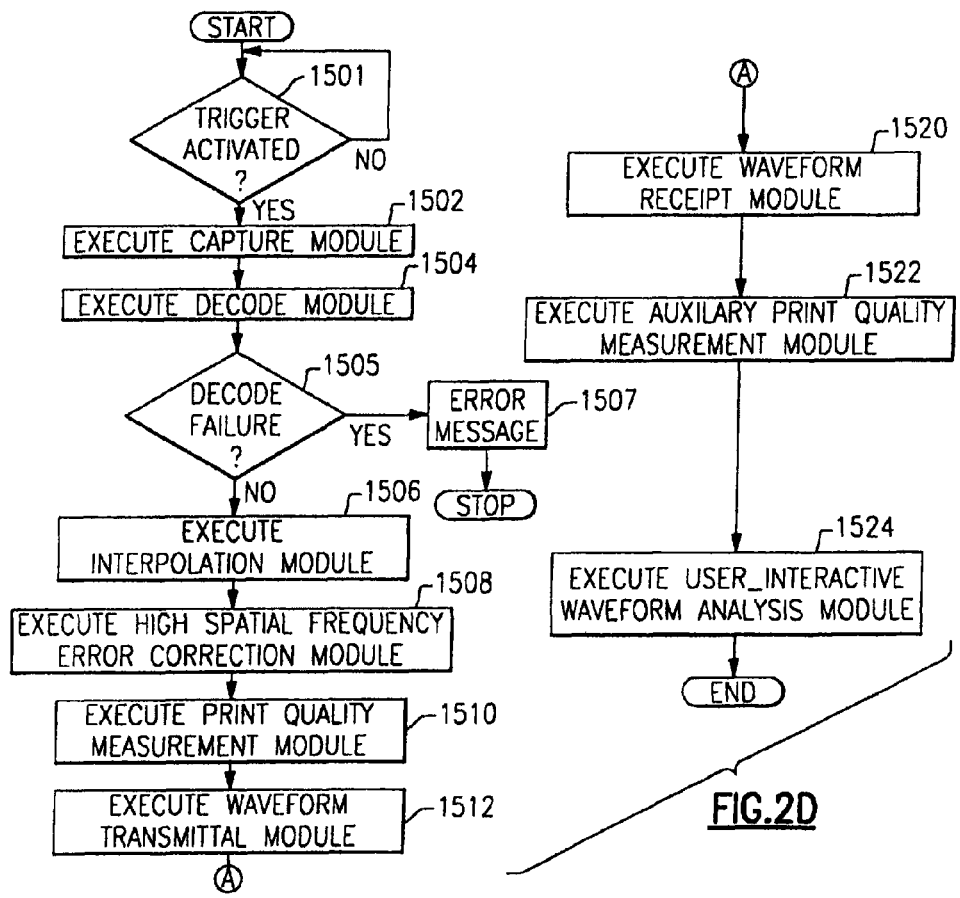
FIG. 2D is a flow diagram illustrating an ordering of processing modules which may be executed by a verification system according to the invention.

Reference is now made to FIG. 2D showing the flow of execution of processing modules by system 1400 in response to trigger 150 being actuated.

At block 1502, control circuit 1010 executes processing module 1402 to capture a frame of image data. The frame of image data may be 1D frame of image data or a 2D frame of image data. In one embodiment the frame of image data comprises gray scale pixel values. A 1D frame of image data may comprise an M×1 array of gray scale pixel values or an M×N frame of image data where N>>M. e.g., a 2000×2 pixel value frame of image data. A 2D frame of image data may comprise an M×N frame of image data, where M, N>100. The frame of image data captured at block 150 can also include color-indicating pixel values. The frame of image data captured at block 1502 normally has a number of pixel values equal to the number of pixels of image sensor 1060. Further, each pixel value in the frame of image data captured by execution of module 1402 normally has an associated position value, corresponding to a discrete pixel position of image sensor 1060. For example, where image sensor 1060 is an image sensor having M column and N rows of pixels, a frame of image data captured at block 1502 may have an M×N array of pixel values, each having a position value corresponding to a certain pixel of image sensor 1066, and each pixel value representing light incident at a discrete location on substrate, s. Where image sensor 1060 is an M×1 image sensor having a single row of pixels, the frame of image data captured at block 1502 may have an M×1 array of pixel values, each pixel value having a pixel value position corresponding to a pixel of image sensor 1060 and each pixel value representing light incident at a discrete location on substrate, s. It is understood that the capture of a frame of image data at block 1402 that is subject to further processing, control circuit 1010 may capture a plurality of parameter-determining frames of image data for purposes of establishing e.g., exposure parameters.

Figure 2E:
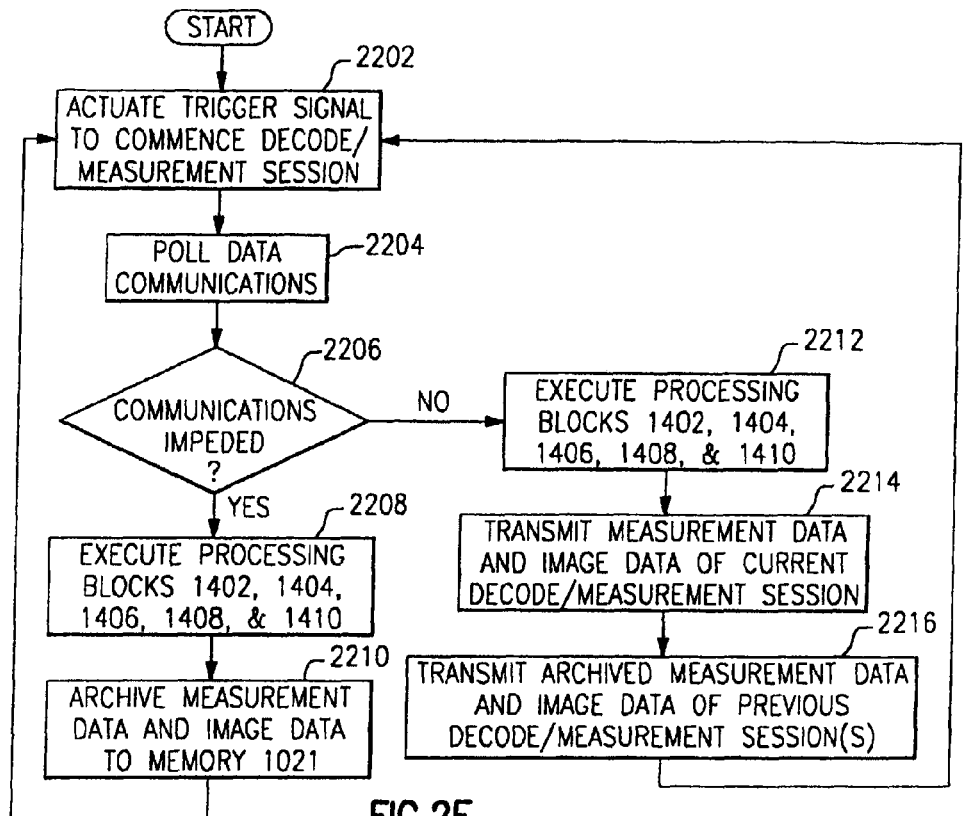
FIG. 2E is a flow diagram illustrating operation of a verification device according to the invention in one mode of operation.

When executing image capture module 1402 control circuit 1010 may automatically correct image signals generated by image sensor 1060 for fixed pattern noise. Specifically, during execution of module 1402 control circuit 1010 may correct image signals of image sensor 1060 for fixed pattern noise that is attributable to nonuniformities of a projected illumination pattern projected by an illumination assembly 1041 of device 100. Referring to FIG. 6B, device 100 may include an illumination assembly 1041 including at least one light source such as LEDs 1082 which projects illumination pattern, P, onto substrate, s. However, due to inconsistencies in e.g. the illumination output, degradation level, and spacing between each individual LED 1082, the illumination pattern, P, projected onto substrate, s, will not be completely uniform. FIG. 2F shows a scan reflectance profile for a linear image corresponding to an area of substrate, s, illumination by illumination system 1041, where substrate, s, is of uniform gray scale. It is seen that because the irradiance level is not uniform, an electronic image corresponding to region of substrate, s, will be affected by fixed pattern noise attributable to radiance nonuniformities of pattern, P.

Accordingly, device 100 may be configured to operate in a calibration mode in which device 100 establishes correction values for signals generated by image sensor 1060. A calibration mode may be selected, e.g. by decoding with use of device 100 a specially encoded programming bar code symbol, B, which when recognized by device 100 causes device 100 to operate in a calibration mode. Device 100 may also be configured so that a calibration mode is commenced when a control button is actuated. The control button may be, e.g. a physical button on device 100 or on a device spaced apart from device 100, e.g. keyboard 1210K (FIG. 5A). The button may also be a virtual control button displayed on a display of, e.g. device 100 or host processor assembly 1210, as is indicated by calibrate button 2320 shown in FIG. 5L.

Figure 2G:
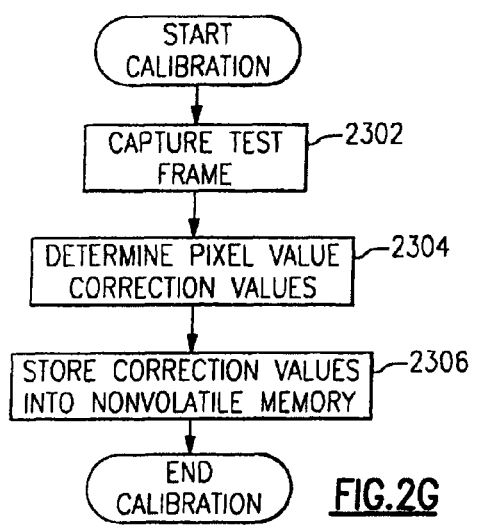
FIG. 2G is a flow diagram of a verification device according to the invention in a calibration mode of operation.
Figure 2F:
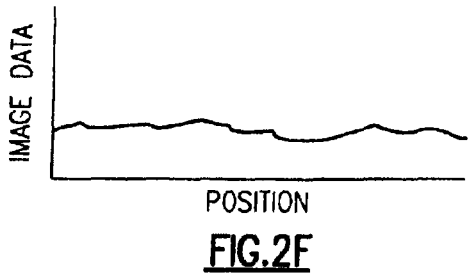
FIG. 2F is a diagram illustrating a set of image data including fixed pattern noise.

When operating in a fixed pattern noise calibration mode, control circuit 1010 may operate in accordance with the flow diagram of FIG. 2G. At block 2302 control circuit 1010 captures a test frame of image data. Typically, at block 2302 control circuit 1010 captures an image representation of a uniform gray scale substrate, s, such as a white sheet of paper. Illumination assembly 1041 is controlled to be energized while the test frame is captured at block 2302 in such manner that the image data represents the radiance nonuniformities of pattern, P. At block 2304 control circuit 1010 determines correction values for correcting image signals of image sensor 1060. In one embodiment, control circuit 1010 at block 2304 calculates correction pixel values for each pixel position of the test frame captured at block 2302. The correction pixel values determined at block 2304 are determined such that when scaled by its corresponding calculated correction pixel value, each pixel position of the corrected image has an equal gray scale value. At block 2306 control circuit 1010 stores the determined pixel correction values into a nonvolatile memory device such as EROM 1022. By storing the values into a nonvolatile memory device 1022 the correction values are retained after device 100 is powered down. It will be seen that the calculated correction values will correct for fixed pattern noise attributable to sources other than illumination assembly 1041, e.g. lens 1070 and image sensor 1060.

Device 100 may include hardware elements that appropriately boost or reduce the amplitude of image signals output from image sensor 1060 in accordance with correction values determine at block 2304. Alternatively, control circuit 1010 may correct image data in accordance with stored fixed pattern noise correction values by scaling pixel values of a preliminary memory-stored frame of image data in accordance with stored pixel correction values after the preliminary frame of image data is stored into RAM 1021.

It may be desirable to operate device 100 in accordance with the calibration mode several times during the lifetime of device 100. Device 100 may require fixed pattern noise calibration, for example, if some of LEDs 1082 become degraded due to age, or if one or more of LEDs 1082 becomes non-functional.

At block 1504, control circuit 1010 executes decoding module 1404 to attempt to decode a bar code. Information respecting various reference bar code decoding routines is available from the Association for Automatic Identification and Mobility ("AIM"), at www.aimglobal.org. Information respecting various bar code decoding routines is also available in various standards published by the International Standards Organization ("ISO"). When device 100 successfully decodes a bar code, device 100 stores a decoded out message at a memory location of device 100. If at block 1505 device 100 determines that bar code decoding is not successful, device 100 outputs an error message at block 1507 (such as a read failure message to display 1210*d* of host processor assembly 1210 or display 194 of device) and waits for a next trigger actuation. Alternatively, after attempting to decode a bar code symbol at block 1504, control circuit 1010 may proceed directly to block 1506 whether or not a decode attempt at block 1504 is successful. Device 100 may be configured so that device 100 actuates green LEDs 1052 if decoding is successful at block 1504. Device may also be configured so that device 100 actuates red LEDs 1051 if decoded at block 1505 is not successful. Device may also be configured to actuate acoustic output 1053 if decoding is successful. Referring to FIG. 6A, an operator can observe light from LEDs 1051 and 1052 by viewing through window 11354 into an interior of housing 1100.

Figure 3A:
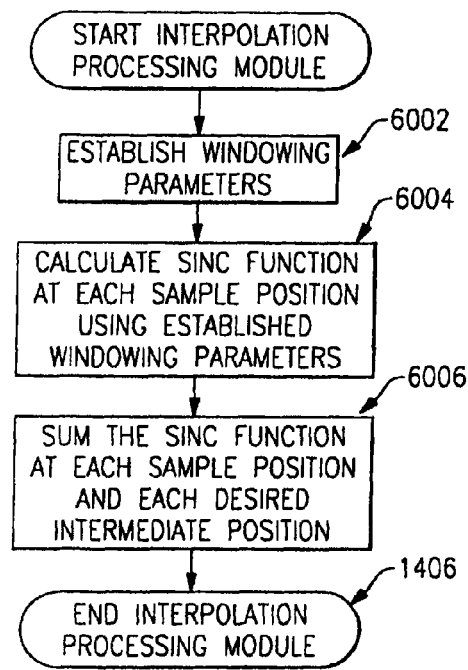
FIG. 3A is a flow diagram illustrating steps which may be taken by a device according to the invention pursuant to execution of an interpolation module.
Figure 3H:
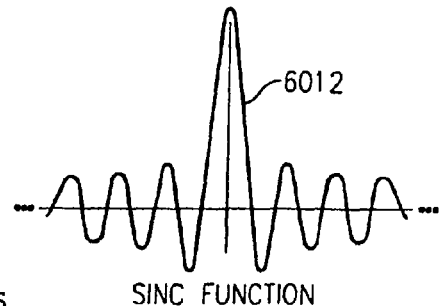
FIGS. 3H-3L are diagrams illustrating operation of an interpolation module according to the invention.
Figure 3I:
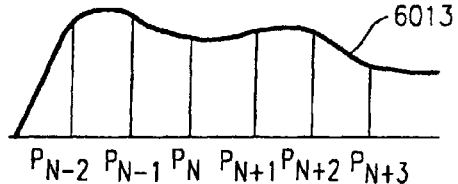
Figure 3K:
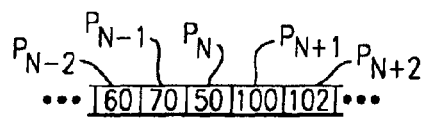

At block 1506 control circuit 1010 executes interpolation module 1406. By execution of interpolation module 1406 control circuit 1010 determines constructed pixel values for interpolated pixel positions intermediate "actual" pixel positions of a frame of image data. Control circuit 1010 can interpolate one or more constructed pixel values between each "actual" pixel value that corresponds to a position of an individual pixel of image sensor 1060. In one embodiment, control circuit 1010 interpolates constructed pixel values from actual pixel values by way of a process of linear interpolation. In executing a linear "straight line" interpolation process relative to a linear gray scale image, control circuit 1010 may determine that a constructed pixel position intermediate adjacent actual pixel positions having gray scale values of 50 gray scale and 100 gray scale, should have a value of 75 gray scale. FIG. 3I shows a representation of a reference reflectance profile 6013 representing the image on substrate, s, which is sampled at pixel positions $P_{N-2}$ through $P_{N+3}$. In a particular example, control circuit 1010 may process the gray scale linear frame of image data represented in FIG. 3K, wherein $P_{N-1}$, $P_N$, $P_{N+1}$ represent original pixel value positions of an input one dimensional frame of image data, each corresponding to an individual pixel of image sensor 1060, and wherein the pixel positions have the gray scale pixel values ( . . . , 70, 50, 100 . . . ) indicated. In executing interpolating interpolation module 1406, control circuit 110 produces the enhanced resolution gray scale frame of image data indicated by FIG. 3L. The frame of image data represented by FIG. 3I includes having gray scale pixel values calculated by way of linear interpolation for interpolated pixel positions, I, intermediate actual pixel positions. In executing module 1406, control circuit 1010 develops an electronic representation of a bar code symbol that more accurately represents the characteristics of the printed bar code symbol printed on substrate, s, than the originally captured image captured at block 1502.

Figure 3J:
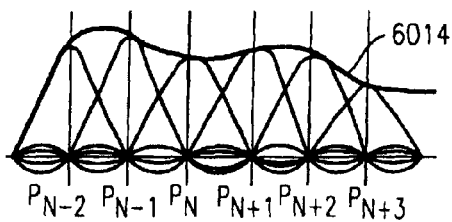
Figure 3L:
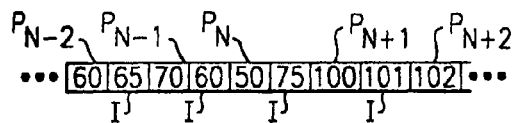

Constructed pixel values for interpolated pixel positions intermediate of original pixel positions (e.g., "actual" pixel positions having values corresponding to light on an individual pixel of sensor 1060) can also be calculated with utilization of a non-linear interpolation process. An example of the invention wherein control circuit 1010 utilizes a sinc function to calculate constructed pixel values at interpolated pixel positions intermediate actual pixel position is described with reference to FIG. 3A. At block 6004, control circuit 1010 calculates sinc functions at each sample position (e.g. for each pixel position having a pixel value). The result of processing block 6004 is described with reference to the waveforms diagrams of FIGS. 3H, 3I, and 3J. The sinc function given by the formula sinc (x)=sinc x/x at any given sample position has the characteristics represented by waveform 6012 (FIG. 3H). Superimposed sinc function waveforms for several sample positions are shown in FIG. 3J. At block 6006, control circuit 1010 sums the sinc function at each sample position and each desired interpolated position. The resulting smoothed waveform 6014 (FIG. 3J) represents the result of interpolating sample values at a very large number of interpolated positions. It will be seen that processing speed can be increased by calculating constructed sample (e.g. pixel) values for fewer numbers of interpolated sample positions. Processing speed can also be increased by establishing windowing parameters that modify each sinc function so that each determined sinc function contributes to the calculated value of a fewer number of interpolated sample positions. Referring to the flow diagram of FIG. 3A, control circuit 1010 at block 6002 may establish windowing parameters and at block 6004, control circuit 1010 may calculate sinc functions utilizing the windowing parameters established at block 6002. With reference to FIG. 3J, it is seen that without establishing windowing parameters, a sinc function for each sample position would produce a value contributing to the calculated constructed sample value at each interpolated sample position. That is, in an initial sample having 1024 pixel values corresponding to a row of pixels and where it is desired to calculate a single interpolated pixel value intermediate each original pixel value, control circuit 1010 would sum 1024 sinc function values for each interpolated pixel position.

Referring again to the flow diagram of FIG. 3A control circuit 1010 at block 6002 may establish simple threshold windowing parameters which discard sinc function values below a predetermined value. Sinc function values may also be discarded with use of a peak limiting function which discards a predetermined number of peaks of a sinc function waveform. Control circuit 1010 may also at block 6002 modify a sinc function utilizing an exponential function. With utilization of an exponential function, windowing parameters can be established which substantially reduce the time required for calculation of a constructed sample value without substantial reduction of information contained in an original set of sinc function waveforms. Further aspects of an embodiment of interpolation module 1406 are described in connection with Example 1 herein below. In Example 1, a transfer function executed by control circuit 1010 when executing interpolation module 1406 includes a sinc function and an exponential function, the exponential function reducing the number of interpolated sample positions for which the sinc function for a given sample position contributes a value.

EXAMPLE 1

Figure 3B:
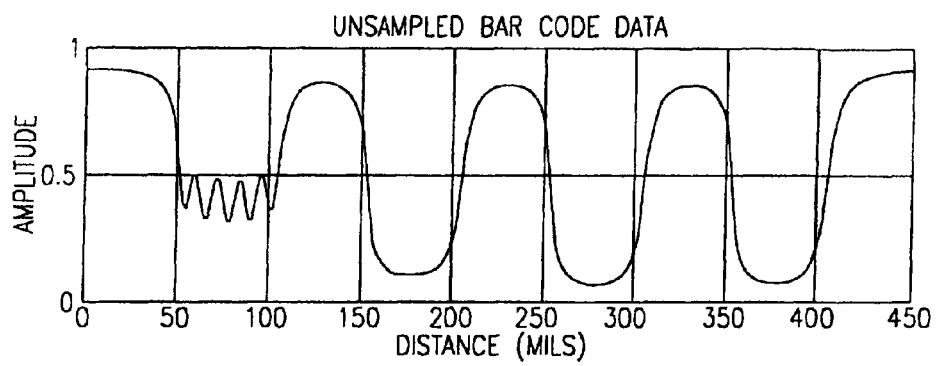
FIGS. 3B-3G are a series of waveform diagrams illustrating operation of a device according to the invention while executing an interpolation module.
Figure 3C:
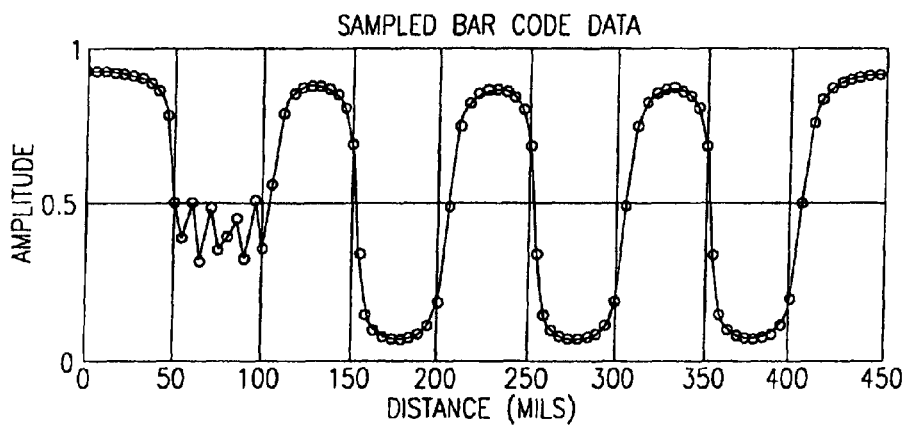

An under sampled signal is processed. The initial bar code data prior to sampling is represented in the waveform diagram of FIG. 3B. The waveform of FIG. 3B is then sampled with sample spacing of Period2. The waveform diagram presented in FIG. 3B is a scan reflectance profile in which image data sample values are expressed in terms of ratio to maximum values. In the present example, a larger number corresponds to a higher reflectance, i.e., white is high. The sampled bar code data is shown in FIG. 3C with each sample point noted.

A sinc function is given by eq. 1-1 below, wherein a functional definition of the sinc function is conditional to avoid the singularity at 0.

$$sinc(x) := \text{if}\left[(x) = 0, 1, \frac{\sin(\pi \cdot x)}{\pi \cdot x}\right] \quad \text{(eq. 1-1)}$$

Figure 3D:
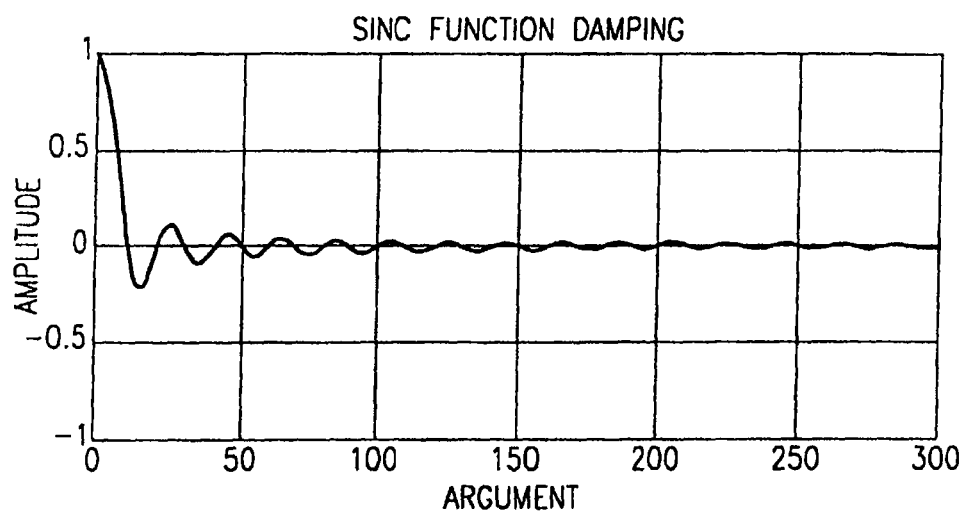
Figure 3E:
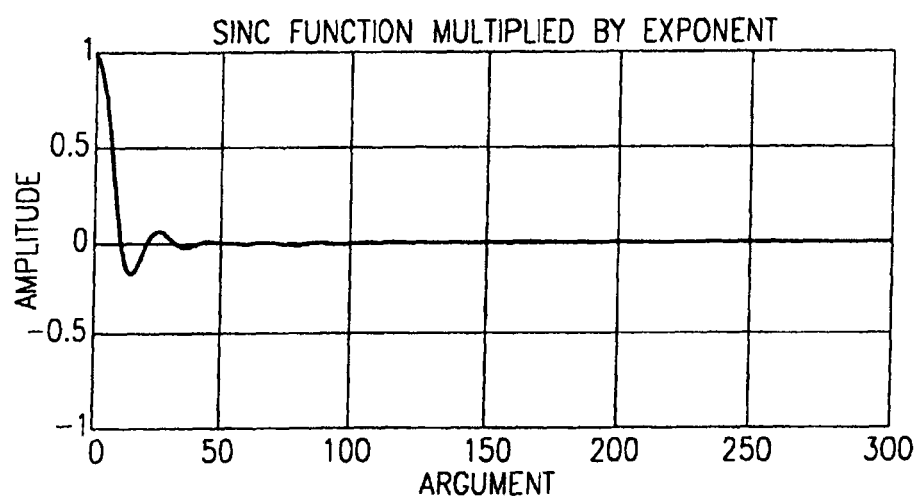

A waveform diagram wherein values generated in accordance with the sinc function given by eq. 1-1 is presented in FIG. 3D. It is seen from the waveform diagram of FIG. 3D that the transfer function given by eq. 1-1 exhibits a decay such that hundreds of terms in a series expansion might be needed in order to converge with reasonable precision. FIG. 3E is a waveform diagram representing a sinc function modified utilizing an exponential function windowing parameter. The transfer function represented by the waveform diagram of FIG. 3E includes a sinc function term multiplied by an exponential decay term. Sinc function terms (modified by the exponential decay function) below predetermined amplitudes can be discarded without significant loss of signal reconstruction accuracy. Modified sinc function terms modified with an exponential damping function can be discarded by way of subjecting the modified sinc function to a simple threshold procedure to eliminate values below a predetermined near-zero value. The summation in Example 1 is truncated after about 60 terms. It is seen that the processing speed can be increased by establishing an appropriate windowing parameter.

The 6 mil (1 mil=1/1000 inch) narrow element width sampled bar code data presented by the waveform diagram of FIG. 3C is at 5 mil intervals.

Constructed sample values are calculated from sample data presented in FIG. 3C utilizing a series of sinc functions. Sampling spacing of interpolated sample values is set to 1 mil per sample. A sinc function argument is given by eq. 1-2 through eq. 1-4 as follows:

$$Period2 = 5.0 \text{ mils} \quad \text{(eq. 1-2)}$$

$$fs := \frac{1}{Period2} \quad \text{(eq. 1-3)}$$

$$\omega c := 2 \cdot \pi \cdot \frac{fs}{2} \quad \text{(eq. 1-4)}$$

Where ωc, the frequency of the sinc function argument, is given by ωc=0.628. An exponential windowing function is established as follows:

$$a = 5 \quad \text{(eq. 1-5)}$$

$$Ex(k) := e^{-\left(\frac{k}{a}\right)^2} \quad \text{(eq. 1-6)}$$

Where a is the exponential damping factor. A series expansion, where sum is the extent of the summation, for use in reconstructing the waveform values at the interpolated sample positions with separation DataSep:=1 is as follows:

$$xr(t) := \sum^{\text{floor}\left(\frac{t+\frac{sum}{2}}{Period2}\right)} BS(n \cdot DataSep) \cdot Period2 \cdot \frac{\omega C}{\pi} \cdot$$

$$sinc\left[\omega c \cdot \frac{(t - n \cdot Period2)}{\pi}\right] \cdot Ex\left[\omega c \cdot \frac{(t - n \cdot Period2)}{\pi}\right]$$

$$n = \text{floor}\left(\frac{t - \frac{sum}{2}}{Period2}\right)$$

(eq. 1-7)

Figure 3F:
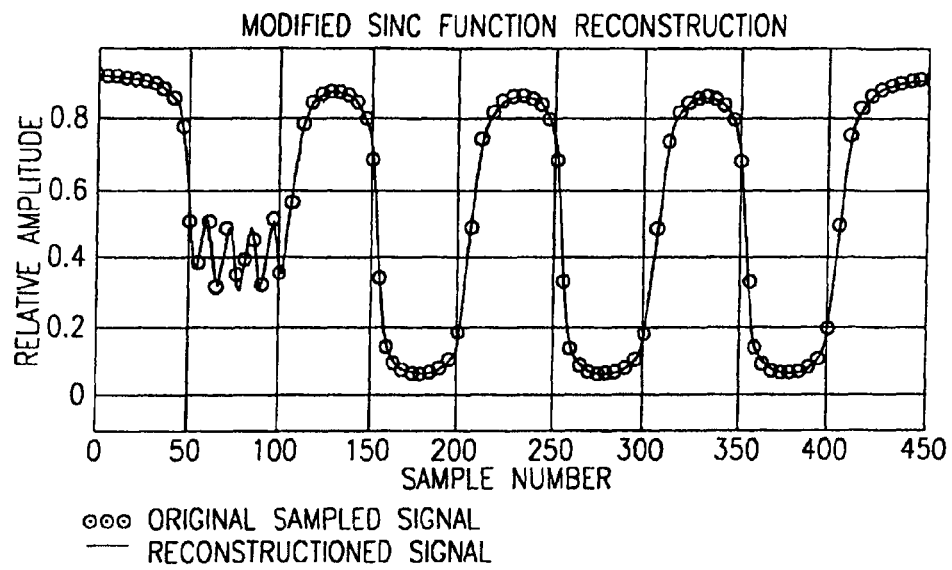
Figure 3G:
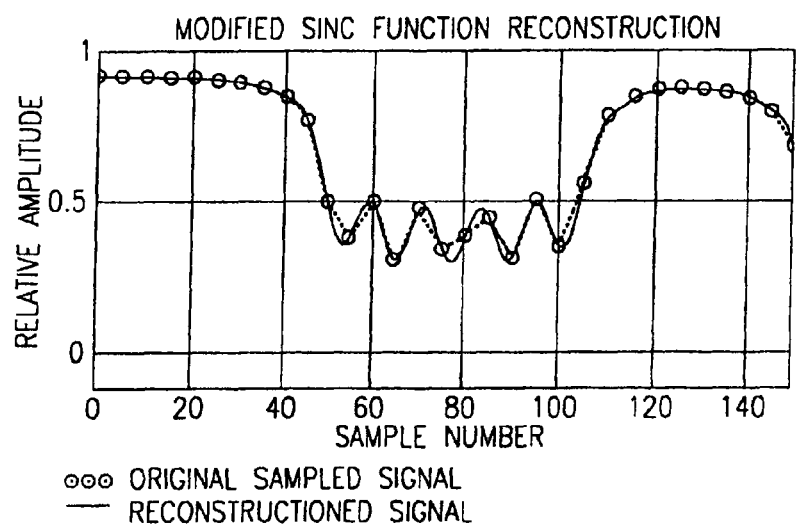

In accordance with the transfer function of eq. 1-7 a waveform will be reconstructed with samples at 1 mil intervals. Segments of the output waveform resulting from subjecting the input waveform of FIG. 3C to the transfer function of eq. 1-7, where period2=5.0 mils, a=2.5 mils and sum=60 are presented in FIGS. 3F and 3G. FIG. 3F illustrates the interpolated or reconstructed waveform from sample numbers 0-450 while FIG. 3G illustrates the interpolated waveform from sample numbers 0-145.

Accordingly, it is seen that a bandwidth limited signal that is sampled can be reconstructed with improved precision using an appropriately dimensioned series of sinc functions. An exponential window parameter or function can significantly reduce the number of terms in the series without significantly impacting the accuracy of the reconstructed waveform.

Figure 4A:
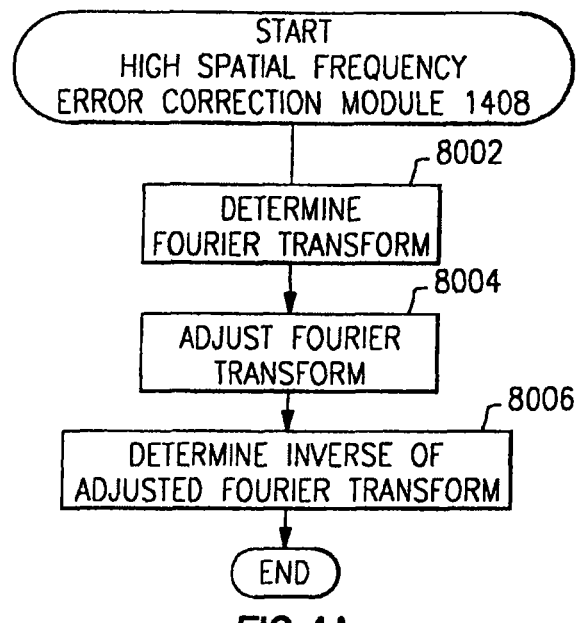
FIG. 4A is a flow diagram illustrating steps which may be taken by a device according to the invention pursuant to execution of a high spatial frequency correction module according to the invention.

At block 1508 control circuit 1010 executes high spatial frequency error correction module 1408. Device 100 may include a lens 1070 that has an approximately linear modulation transfer function (MTF) fall off with spatial frequency. Accordingly, device 100 may exhibit reduced optical resolution and edge contrast at higher spatial frequencies. In order to correct for reduced optical resolution at higher frequencies, a frame of image data may be subject to the processing that is described with reference to the flow diagram of FIG. 4a. At block 8002 control circuit 1010 determines the Fourier transform of an input linear gray scale pixel image (e.g. an M×1) array of pixel values. The image data input at block 8002 may be the enhanced resolution image data output by control circuit 1010 when executing interpolation module 1406, or may be the image data captured by control circuit 1010 pursuant to execution of image capture module 1402, if for example interpolation module 1404 is not executed or not executed prior to execution of module 1408. Determining the Fourier transform of a gray scale pixel image expresses the original space-domain image information in the frequency domain. At block 8004 control circuit 1010 subjects the Fourier transform determined at block 8002 to an adjustment process which may comprise a vector multiplication function. For example, at block 8004 control circuit 1010 may multiply the Fourier transform determined at block 8002 in accordance with an appropriately defined straight line gain as a function of frequency as is explained with reference to Example 2. Subjecting at block 8004 the Fourier transform determined at block 8002 to an appropriate multiplication function increases the amplitude of the Fourier transform at certain frequency components without substantially affecting the amplitude of the Fourier transform at other frequency components. Control circuit 1010 at block 8006 converts the adjusted Fourier transform to the space domain by determining the inverse of the adjusted Fourier transform that has been adjusted at block 8004. In executing module 1408 control circuit 1010 develops an electronic representation of a bar code symbol that more accurately represents the characteristics of the printed bar code symbol printed on substrate, s, than the originally captured image captured at block 1502. Although the implementation shown relies upon the use of the Fourier transform, alternate transforms might also be utilized, such as sine, cosine, wavelet or Laplace transforms.

Those skilled in the art will recognize that enhancement of the higher spatial frequencies, as implemented in module 1408 by control circuit 1010, could also be accomplished using a number of alternate techniques, many of which would not require the use of Fourier transform techniques. Examples are properly defined and dimensioned FIR (Finite Impulse Response) and IIR (Infinite Impulse Response) filters, both of which would be implemented by the control circuit 1010 or in a separate digital processing element (not shown in the drawings) or even by more traditional analogue electronic high pass filters that might be implemented in the analog domain after imager 1060 and prior to the A/D converter 1079 shown in FIG. 2a.

EXAMPLE 2

Figure 4B:
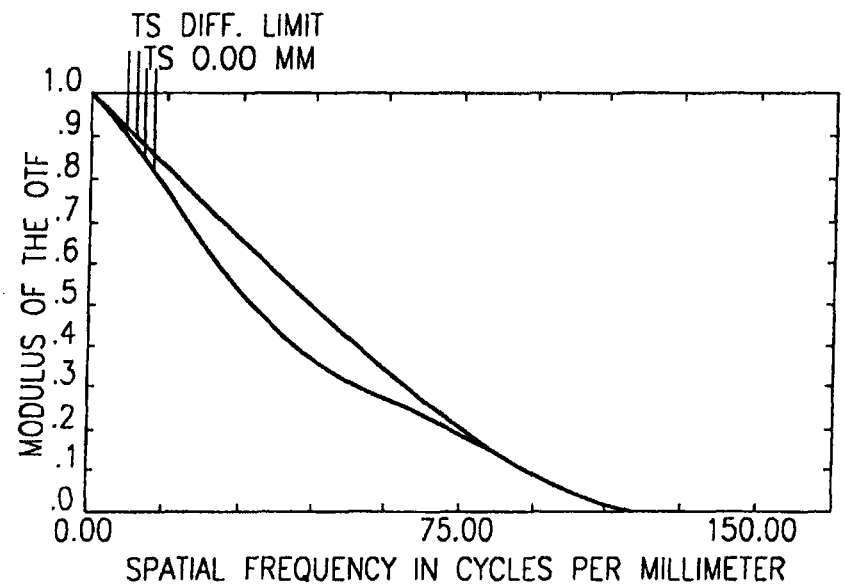
FIG. 4B is an MTF graph for a particular custom lens.

An imaging lens 1070 of device 100 in an embodiment subject to analysis exhibits an approximately linear MTF fall off with spatial frequency. This MTF profile for a custom singlet such as might be used in this product is shown in FIG. 4B. This profile was created using the optics design program ZEMAX from the ZEMAX Development Corporation. The approximately linear MTF fall off of the lens results in reduced optical resolution and edge contrast at the higher spatial frequencies. The present custom lens has an MTF of approximately 71% at 20 cycles per mm in imager space. This optical pattern is imaged on a one dimensional CCD image sensor converting the optical representation of the bar code pattern under test to an electrical waveform. In an analogous fashion, the electrical signal exhibits an approximately linear fall off with frequency in the electrical domain.

Figure 4C:
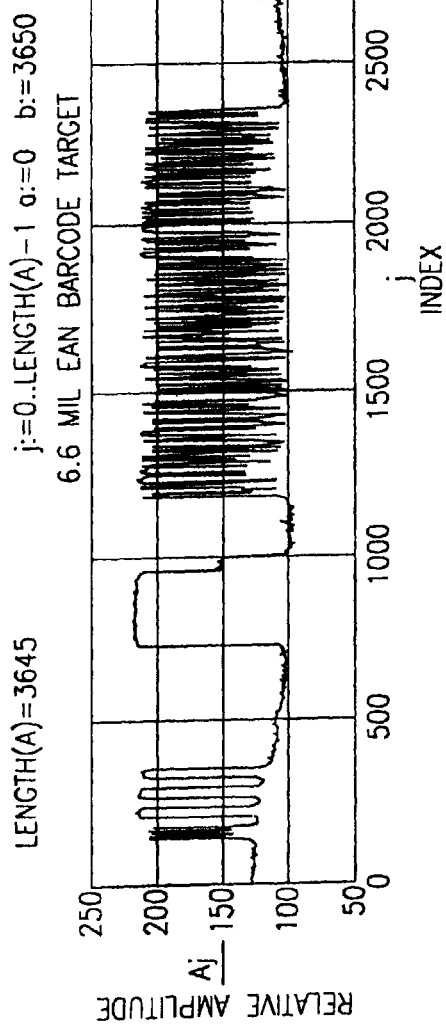

An EAN128 999999/R1 symbol is sampled by capturing a 1D frame of image data. The file length of the input signal is 3,646 elements (gray scale pixel values) long. The original EAN bar code signal is represented in the center portion of FIG. 4C. FIG. 4C shows a scan reflectance profile of an EAN bar code symbol with an average narrow element width of 6.6 mils. At each end of the field of view 1.8 LP/mm test targets can be seen. It is observed from the scan reference profile of FIG. 4C that increased signal results in a lower count, i.e., white is low.

Figure 4D:
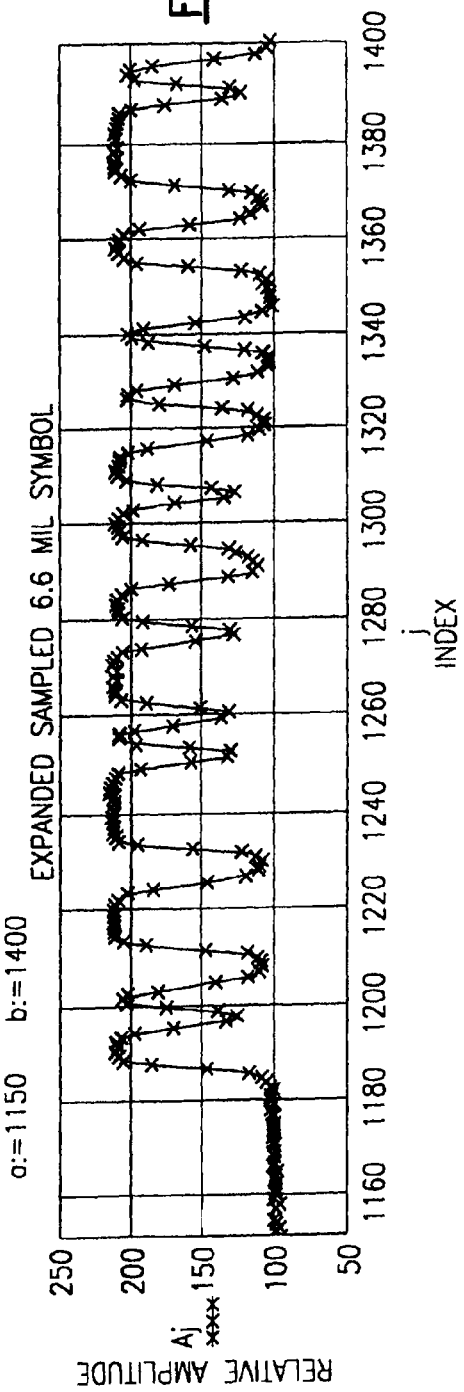

A portion of the sampled data is shown in FIG. 4D with the actual sample points marked. It is observed that the data is adequately sampled at about 4 samples per narrow element.

The result of determining the Fourier transform of the original bar code signal is presented in the waveform diagrams of FIG. 4E and FIG. 4F. FIG. 4E illustrates J index frequency components from 0 to 3500, while FIG. 4F illustrates J index frequency components from 0 to 1000. In this example A represents the scan reflectance profile as shown in FIGS. 4C and B is the Fourier transform of A. Thus, B:=cfft (A).

The Fourier transform of the original input image includes a real and imaginary component. The original file contains 3645 data points and, as a result, the transform file contains 1822 complex elements. Further, the magnitude of the Fourier transform image data is symmetric about the point 1823.

Each CCD pixel has a width of 8 um and the system optical magnification is 5×. Thus, in paper space each pixel spans a width of:

$$\text{Pix} = 0.008 \text{ mm} \quad \text{(eq. 2-1)}$$

$$\text{PixPaper} = \text{Pix} \cdot 5 \quad \text{(eq. 2-2)}$$

$$\text{PixPaper} = 1.575 \times 10^{-3} \text{ in. or } 1.6 \text{ mils} \quad \text{(eq. 2-3)}$$

Accordingly, Scan Width=PixPaper·3645=5.74 in. The frequency span per count, and the full scan frequency span, are given by eq. 2-4 and eq. 2-5 respectively.

$$\frac{1}{ScanWidth} = 6.859 \times 10^{-3} \frac{1}{\text{mm}} \quad \text{(eq. 2-4)}$$

$$\frac{1}{ScanWidth} \cdot 1822 = 12.497 \frac{1}{\text{mm}} \quad \text{(eq. 2-5)}$$

Thus, the largest complete sine cycle that can be scanned would span 5.74 inches in paper space. This corresponding to the lowest detectable frequency in paper space. Thus, in paper space, a single count corresponds to a spatial frequency of $6.859 \times 10^{-3}$ cycles/mm. The full scale span in paper space would therefore be 1822 times this value, or 12.50 cycles per mm.

In this example, the highest spatial frequency of importance in paper space is 4.0 LP/mm (corresponding to a minimum bar code element size of 5.0 mils). Because the optical system has a 5× magnification, this corresponds to a spatial frequency of 20 LP/mm at the image sensor. The lens MTF as seen is FIG. 4B has an MTF of approximately 71% at 20 LP/mm.

From the calculations above, the spatial frequency count associated with 4 LP/mm can be found by dividing 4.0 by the spatial frequency of $6.859 \times 10^{-3}$ cycles/mm.

$$\text{Count} := \frac{4}{6.859 \cdot 10^{-3}} \quad \text{(eq. 2-6)}$$

$$\text{Count} = 583$$

ZEMAX optical modeling software was used to model the optical system of device 100. From the ZEMAX analysis of the optical system, it was observed that 20 cycles per mm in imager space corresponds to 4 cycles per mm in paper space. Also, at this point frequency, the MTF is approximately 0.71. From the calculations above, 4 cycles per mm exhibits an index of 583. To compensate for the reduced MTF of the lens, the gain might be set to 1/0.71=1.41. As an initial value, use a compensation gain g. of 1.00.

A gain function was established as a linear function of frequency. Gain was established to be symmetrical about the point 1822. The gain function, where g=1.0, is expressed by eq. 2-7.

$$g = 1.0 \quad \text{(eq. 2-7)}$$

$$G_j := \text{if} \left[ \begin{array}{l} j \leq 1822, \left(1 + g \cdot \frac{j}{1822}\right), \\ \left(1 + \frac{3644 \cdot g - j \cdot g}{1822}\right) \end{array} \right]$$

Figure 4G:
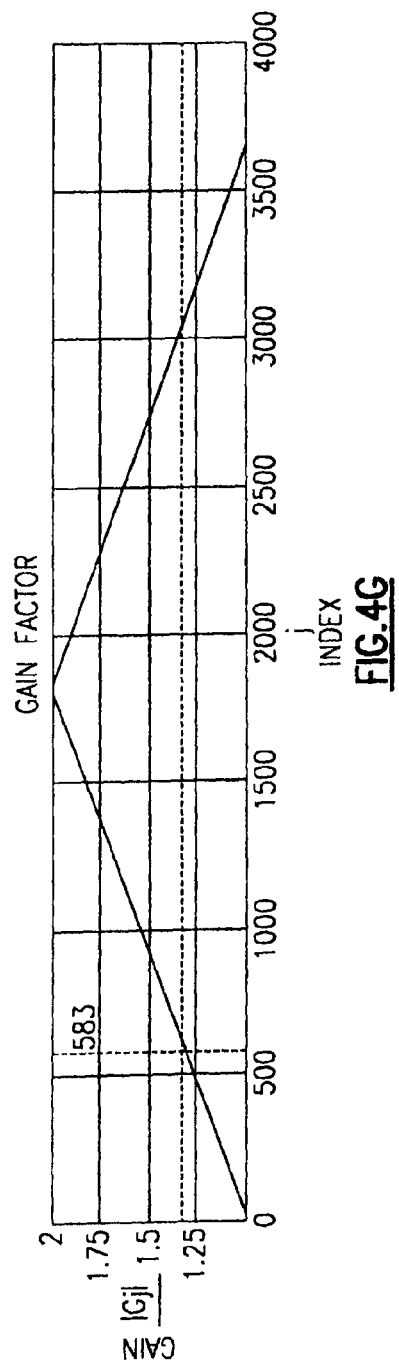

Eq. 2-7 is shown graphically in FIG. 4G. Utilizing the frequency dependent gain function of eq. 2-7, the Fourier transform shown graphically in FIGS. 4E and 4F is adjusted.

This is accomplished by multiplying each complex term of the Fourier transformed input signal by each term of the frequency dependent gain term $G_j$.

$$C_j := G_j \cdot B_j \qquad \text{(eq. 2-8)}$$

The inverse of the adjusted Fourier transform is then determined as represented by the term D below:

$$D := icfft(C) \qquad \text{(eq. 2-9)}$$

Figure 4H:
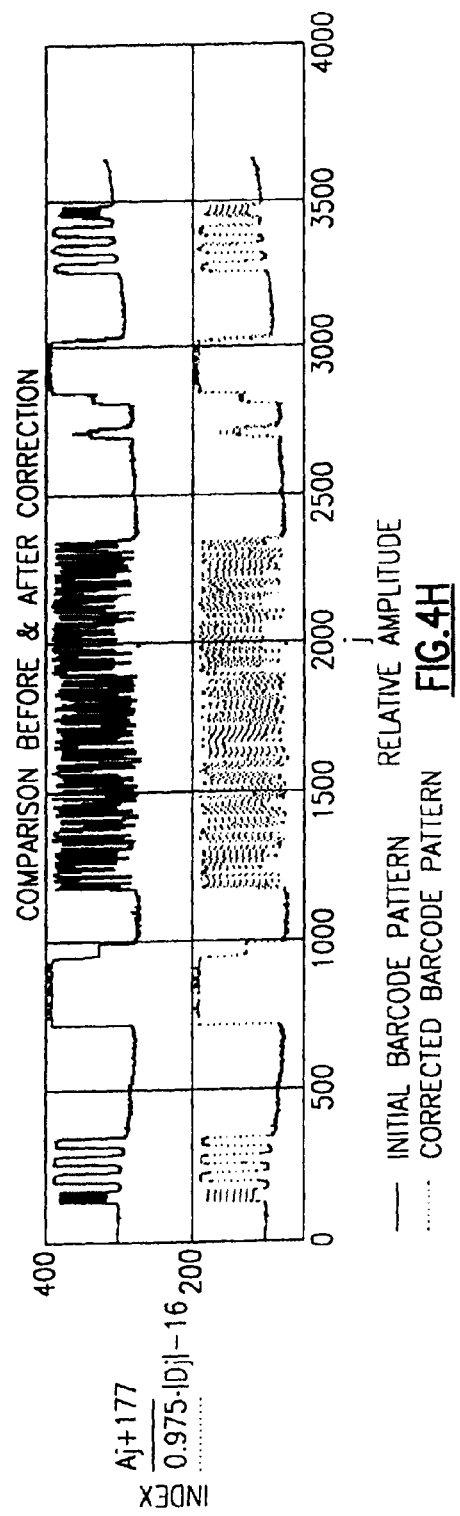
Figure 4K:
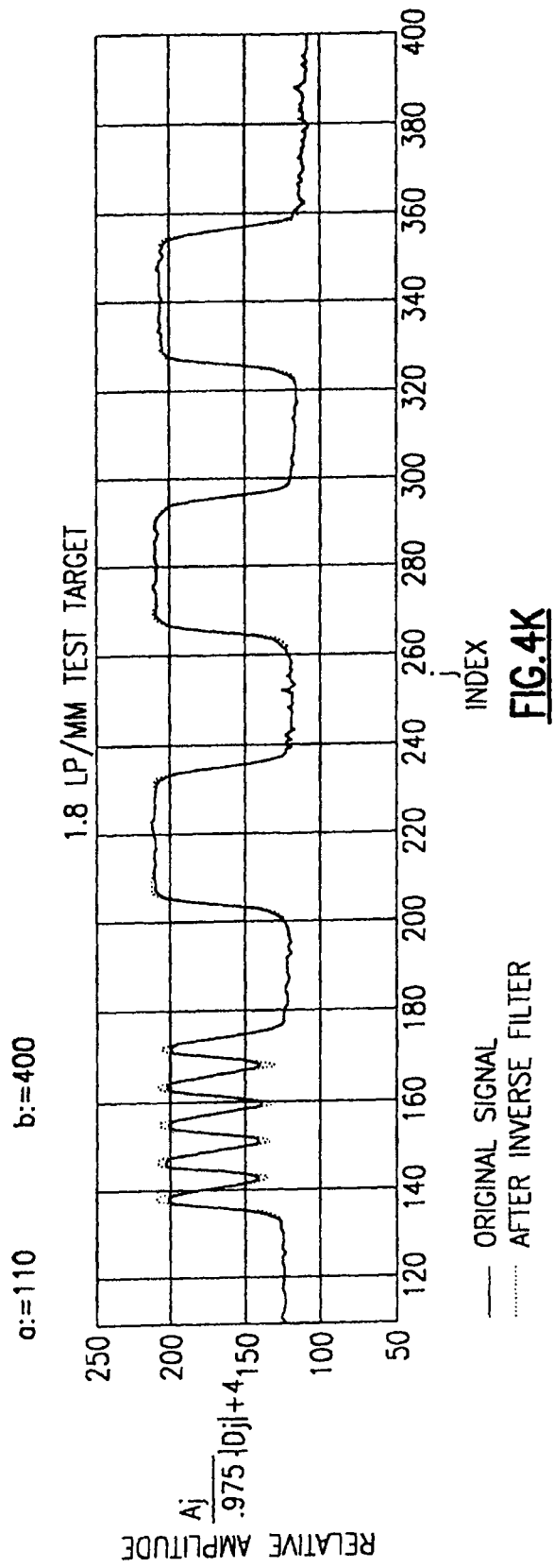

FIGS. 4H-4K illustrate representations of the corrected frame of image data. FIG. 4H illustrates the result of the correction over all pixel positions. FIGS. 4I and 4J illustrate the result of the correction over select ranges of pixel positions. FIG. 4I illustrates the original signal and the signal after high frequency correction. FIG. 4J shows the two waveforms superimposed on one another in order to show the improvement in the high frequency spatial components. The original waveform is shown as the solid line and the improved waveform is the dashed line. FIG. 4K shows the 1.8 LP/mm test target at the extreme left of the field of view. Observe in both FIG. 4J and FIG. 4K that there is a noticeable improvement in the signals associated with the high frequency components without any noticeable distortion degradation visible on the wide bar elements.

The results presented suggested that at least the 6 mil waveform tested can be digitally corrected to compensate for the optical MTF reduction caused by imaging lens 1070. The gain used to implement this correction is approximately that required to compensate for the lens MTF role off at 4 LP/mm in paper space.

While the flow diagram of FIG. 2D illustrates that control circuit 1010 decodes a captured frame of image data in accordance with module 1404 prior to executing interpolation module 1406 and high spatial frequency correction module 1408, control circuit 1010 may execute decode module 1404, automatically in response to receipt of a trigger signal subsequent to execution of interpolation module 1406 and subsequent to the execution of high spatial frequency error correction module 1408 so that enhances image data is processed during decoding. If control circuit 1010 executes the image enhancement interpolation module 1406 and the image enhancement high spatial frequency error correction module 1408 the success rate of the execution of decode module 1404 can be expected to be improved. It will be understood that while modules 1406, 1408 enhance the quality of a captured image, control circuit 1010 may execute only one of modules 1406, 1408 or neither of modules 1406, 1408. Processing modules 1406, 1408 have been described relative to processing of linear image data. Control circuit 1010 may also input 2D image data while executing modules 1406, 1408. Where control circuit 1010 processes linear image data, input image data may be image data representing e.g. light incident on a row of pixels of a one dimensional image sensor, a row of pixels of a 2D image sensor, light incident on a selected row of pixels of a 2D image sensor, or light incident on a transverse line of pixels of a 2D image sensor, such as a diagonal or other transverse straight or curvelinear line of pixels. The input image data input for processing pursuant to the execution of module 1406, 1408 normally comprises pixel data including a plurality of pixel values, each pixel value corresponding to a specific pixel position, wherein each pixel position represents light incident a specific location of target T.

Figure 7A:
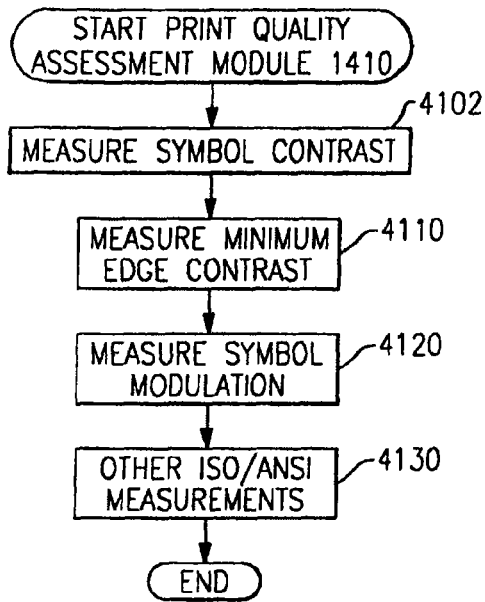
FIGS. 7A-7D are flow diagrams illustrating operation of a device according to the invention during execution of a print quality measurement module.
Figure 7B:
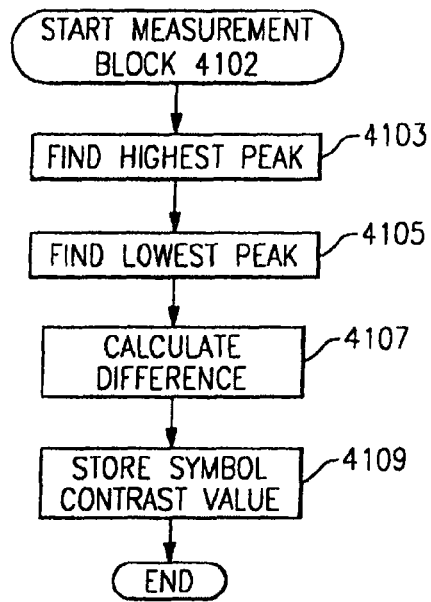

At block 1510 control circuit 1010 executes print quality measurement module 1410 to carry out a series of measurements on the frame of image data that has been processed by interpolation module 1406 and high spatial frequency error correction module 1408 or an unprocessed frame of image data captured at block 1502 if modules 1406, 1408 are deleted. Referring to the flow diagram of FIG. 7A, measurements on the input frame of image data that may be conducted during the execution of block 1510 may include a symbol contrast measurement (block 4102), an edge contrast minimum measurement (block 4110), and modulation measurement (block 4120). Information respecting the above measurement is described in detail in the previously referenced ANSI (X3.182-1990) and ISO (ISO/IEC 15416 and ISO/IEC 15415) Standards (the "ISO/IEC bar code verification specification standards"). In addition to carrying out symbol contrast, edge contrast and, modulation measurements while executing processing module 1410, control circuit 1010 may carry out additional measurements that are in accordance with the above referenced ISO/IEC bar code verification specification standards. With further reference to the execution of processing module 1410 in executing block 4102, and with particular reference to the flow diagram of FIG. 7B control circuit 1010 at block 4103 finds the highest peak of an input scan reflectance waveform. If the input waveform is the corrected waveform 4150 of FIG. 4J the highest peak may be determined to be peak 4150. At block 4105 control circuit 1010 determines the lowest peak of an input scan reflectance waveform, which may be low peak 4153 if the input waveform is the corrected waveform of FIG. 4J. At block 4107 control circuit 1010 calculates the difference between the peak value of the peak identified at block 4103 and the peak value of the peak identified at block 4105. At block 4109 control circuit 1010 stores the calculated symbol contrast measurement calculated at block 4107 into a memory device such as device 1021. Amplitudes of waveform 4150 of FIG. 4 can be expressed in reflectance units (typically a percent of 100% reflectance) by application of a calibration step in which the amplitudes are calibrated with reference to reflectance calibration standards (e.g., one light and one dark).

Figure 7C:
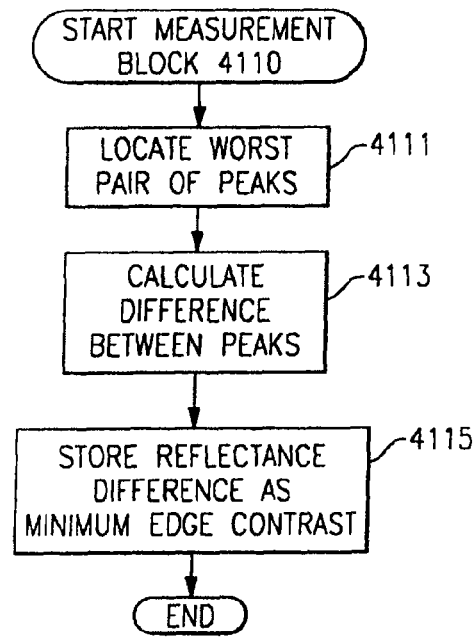

Referring to the flow diagram of FIG. 7C a method for measuring edge contrast is described. At block 4111 control circuit 1010 identifies the worst pair of peaks. Each pair of peak e.g. peak 4155 and peak 4157 of a scan reflectance waveform represents an edge of a bar code symbol. The worst pair of peaks is the pair of peaks having the smallest reflectance difference. The identified worst pair of peaks may represent either a transition from a space to a bar or a transition from a bar to a space. Thus, at block 4111, where the corrected waveform 4150 of FIG. 4J is the input waveform, control circuit 1010 may identify peaks 4159 and peak 4161 as the worst pair of peaks. At block 4113 control circuit 1010 identifies the reflectance difference between the high peak 4159 and the low peak 4161 of the worst pair of peaks identified at block 4111. At block 4115 control circuit 1010 stores the minimum edge contrast value determined at block 4113 into a memory device 100, e.g. RAM 1021.

Figure 7D:
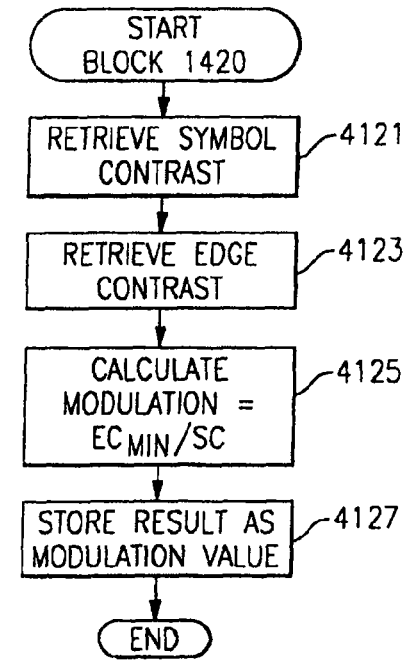

Referring to the flow of diagram of FIG. 7D a method for measuring symbol modulation is described. Modulation is a measurement of the capability of a narrow element of a symbol to be recognized as compared to wide symbol element. At block 4121, control circuit 1010 retrieves the symbol contrast measurement from a memory device 100 that was stored into memory at block 4109. At block 4123 control circuit 1010 retrieves from memory e.g., memory 1021 the minimum edge contrast measurement that was stored into memory at block 4115. At block 4125 control circuit 1010 applies the retrieved values to the formula Modulation=$EC_{MIN}/SC$, where $EC_{MIN}$ is the minimum edge contrast measurement determined at block 4113 and SC is the symbol contrast measurement determined at block 4107. At block 4127 control circuit 1010 stores the resulting modulation measurement into a memory device 100 of system 1400, e.g. memory 1021.

At block 1512 control circuit 1010 executes waveform transmittal module 1412. Specifically at block 1512 control circuit 1010 sends image data such as the processed frame of image data processed by modules 1406, 1408 and/or the captured frame of image data captured by execution of module 1402 to separately housed and spaced apart host processor assembly 1210. Also at block 1512 control circuit sends measurement data resulting from execution of processing module 1410 to host processor assembly 1210. Host processor assembly 1210 then receives the transmitted frame of image data and the measurement data at block 1520 by execution of waveform receive module 1420. As eluded to in connection with FIG. 2A, verification device 100 in executing module 1412 may transmit the waveform wirelessly over a wireless communication link 1500 as is indicated in FIG. 2C.

For determining whether executing waveform transmission module 1412 is appropriate, control circuit 1010 may operate in accordance with the flow diagram of FIG. 2E. At block 2202 control circuit 1010 receives a trigger signal as may be actuated remotely or by actuation of trigger 150 to commence a first decode and measurement session. At block 2204 control circuit 1010 polls data communication components of device such as transceiver 1082 to determine whether device 100 is presently able to send data to a desired destination, e.g. host processor assembly 1210. At block 2206 control circuit 1010 determines whether data communications are currently impeded. Data communication may be impeded, e.g. if device is out of range with respect to a desired data receipt device, e.g. host processor assembly 1210. If data communications are determined to be presently impeded, control circuit 1010 proceeds to block 2208. At block 2208 control circuit 1010 executes processing modules 1402, 1404, 1406, 1408, and 1410 but does not execute waveform transmittal module 1412 to transmit measurement and other data to host processor assembly 1210. Instead, control circuit 1010 proceeds to block 2210 to archive measurement data determined at block 1510, decoded out data message data determined at block 1504 (not mentioned in the FIG. 2E flow diagram) and image data memory, e.g. memory 1021. In archiving data at block 2210, control circuit 1010 stores data in such manner that it can be later uploaded to host processor assembly 1210. Thus, at block 2210 control circuit 1010 may store measurement data, message data, and image data in memory locations other than temporary (sometimes referred to a buffer) memory locations that are continuously written over each time a trigger signal is received. When control circuit 1010 has completed block 2210 control circuit 1010 returns to block 2202 to wait for another decode and measurement session to be commenced by a receipt of a trigger signal.

Referring again to block 2206, if at block 2206 control circuit 1010 determines that data communications between device 100 and host processor assembly 1210 are not impeded, control circuit 1010 proceeds to block 2212. At block 2212, control circuit 1010 executes processing blocks 1402, 1404, 1406, 1408, and 1410. In the execution of block 2212, control circuit 1010 may store data such as image data and measurement data (e.g. symbol contrast, edge contrast, and modulation measurement data) and decoded out message data into buffer memory locations of memory device 1021 for purposes of facilitating an immediate transmission of the data to host processor assembly 1210. However, since host communications are determined to be available, there is no need for control circuit 1010 at block 2212 to archive data into a memory of device 100 in such form that it is available for transmission after a future decode and measurement session. With further reference to the flow diagram of FIG. 2E control circuit 1010 at block 2214 transmits measurement data, decoded message data, and image data of the current decode and measurement session to host processor assembly 1210. The image data referred to in blocks 2210, 2214, and 2216 may be the captured image data captured by execution of module 1402 and/or the processed image data processed in accordance with one or more of modules 1406, 1408. Then at block 2216 control circuit 1010 transmits archived measurement, decoded message data, and image data from previous decode and measurement sessions. Device 100 may be configured so that at block 2216 control circuit 1010 uploads to host processor 1210 all archived measurement, decoded message data, and image data that has been archived by device 100 during each preceding decode and measurement session since the time communications were determined to be impeded. Device 100 can also be configured so that at block 2216 device 100 uploads data from 1 to N previous decode and measurement sessions. Device 100 can be configured so that when archived data is transmitted at block 2216 archive data memory locations of a memory device such as memory 1021 for archiving data pursuant to block 2210 are emptied (e.g. written over with void data). Accordingly, if communications were determined to be unimpeded at block 2206 during an immediately preceding decode and measurement session, control circuit 1010 at block 2216 may after determining that void data is present avoid transmitting archived measurement data, decoded message data, and image data at block 2216 and proceed immediately to block 2202 to wait for a next decode and measurement session to be commenced, by the actuation of a trigger signal.

At block 1522, host processor assembly 1210 executes auxiliary print quality measurement module 1422. In executing auxiliary print quality measurement module 1422 host processor assembly 1210 carries out measurements on the frame of image data transmitted at block 1512 in addition to those measurements performed by control circuit 1010 of verification device 100 pursuant to execution of print quality measurement module 1410. In one example of the invention, device 100 at block 1510 performs a subset of bar code print quality measurements described in the ISO/IEC Bar Code Verification Standards, and at block 1522 host processor assembly 1210 performs additional bar code print quality measurements described in the ISO/IEC Bar Code Verification Standards.

At block 1524, host processor assembly 1210 executes user-interactive waveform analysis module 1424. In executing user interactive waveform assessment module 1424 host processor assembly 1210 causes a graphical representation corresponding to the waveform or image frame transmitted at block 1512 to appear on display 1210d of host processor assembly 1210. The graphical display of image data typically comprises a scan reflectance profile, which is a graphical representation readily determined from a gray scale image map. When gray scale pixel values corresponding to positionally adjacent pixel positions are plotted in graph, the graph (when representing a bar code) has a generally sinusoidal waveform, and is known as a scan reflectance profile. The graphical display by host processor assembly 1210 of a scan reflectance profile by host processor assembly 1210 provides significant advantages. In certain instances, characteristics of a printed bar code symbol can readily be determined by observation of a displayed scan reflectance profile that cannot easily be determined by observation of numerical measurement values. In addition to displaying a graphical representation of the transmitted image, host processor assembly 1210 by execution of module 1424 may, with use of a graphical user interface (GUI), make a variety of user selectable options available for selection by a user. Such option may include, for example, display of the result of the measurements made by verification device 100 during execution of module 1410, and display of the result of the measurements made by host processor assembly 1210 during execution of module 1422.

A physical form view of the system 1400 schematically depicted in FIG. 2C is shown in FIG. 5A. In the embodiment of FIG. 5A host processor assembly 1210 is provided by a desk top personal computer PC 1210-1 having a graphical user interface (GUI). The graphical user interface includes a pointer 1652 which is manipulated into a variety of positions of display 1210d by an operator. While the pointer controller of host processor assembly 1210 in the embodiment shown includes a mouse 1654 for moving pointer 1652, another type of pointer controller (e.g. a trackball, a navigation matrix) may be used. A user moves pointer 1652 between various icons 1662, 1664, 1666 corresponding to various control options. Keyboard 1210k may also be utilized to move pointer 1652.

Figure 5G:
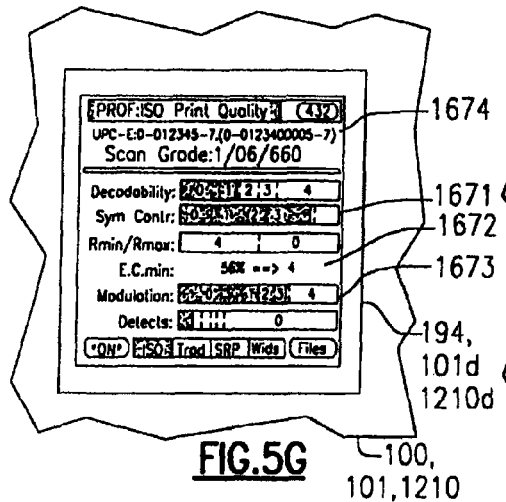
FIGS. 5G-5L are screen shots illustrating user-interactive GUI display screens which may be displayed on a display during execution of a user-interactive waveform analysis processing module according to the invention.

In the example of FIG. 5A, host processor assembly 1210 operates in a mode in which host processor assembly 1210 displays on display 1210d a scan reflectance profile 1670, enabling an operator to view a graphical waveform representation of input image data. The mode of operation depicted in FIG. 5A had previously been entered into by the selection of a scan reflectance profile control button 1666 labels "SRP." With reference to FIG. 5G, another mode of operation of host processor assembly 1210 is depicted. As shown in FIG. 5G, host processor assembly 1210 displays on display 1210d various bar code pint quality measurement data. The mode of operation depicted in FIG. 5G is entered into by selection of control button 1662. In the mode of operation depicted in FIG. 5G, host processor assembly displays symbol contrast measurement data, as calculated at block 4107, edge contrast data 1672 as calculated at block 4113 and modulation data 1673 as calculated at block 4125. While the modes of operation in which host processor assembly 1210 displays on display 1210d a scan reflectance profile 1670 and the mode in which host processor assembly 1210 displays measurement data are depicted as occurring sequentially in response to user input, they can also occur simultaneously. For example in the embodiment of FIG. 5L, host processor assembly 1210 simultaneously displays a scan reflectance profile 1670 and edge contrast measurement data 1672. Host processor assembly 1210 also may have a mode of operation in which decoded bar code data 1674, as shown in FIG. 5A and FIGS. 5G-5J decoded at block 1404 is displayed.

Reference is now made to FIG. 5e, in which another embodiment of the invention is shown. The portable data terminal of FIG. 5E has the processing module integration scheme as depicted in FIG. 8A. Portable data terminal 101 has processing modules 1402, 1404, 1406, 1408, 1410, 1422 and 1424 integrated therein. As indicated previously, an imaging assembly 1040 as well as the other components described in connection with FIG. 2A may be incorporated within hand held portable data terminal 101 and may be encapsulated by housing 101h. Processing modules 1402, 1404, 1406, 1408, 1410, 1422 and 1424 in the embodiment of FIG. 5E are contained within hand held housing 101h. Incorporating all of processing modules 1402, 1404, 1406, 1408, 1410, 1422 and 1424 within a single hand held unit provides certain advantages. In the embodiment of FIG. 5E, waveform transmittal modules 1412 and receipt module 1420 are not needed. Accordingly, the embodiment of FIG. 5E does not require data communications circuitry for communicating data between spaced apart devices. Referring to further aspects of portable data terminal 101, portable data terminal 101 includes a keyboard 101k a trigger button 150 and a pointer controller shown as being provided by a navigation matrix 1655. In execution of user-interactive waveform analysis module 1424, portable data terminal 101 may display on display 101d any one of the display formats depicted in FIGS. 5G-5L. Because the screen formats of FIGS. 5G-5L may be displayed by host processor 1210 or by portable data terminal 101 configured in accordance with the integration scheme of FIG. 8A, the devices depicted in FIGS. 5G-5L are labeled with the portable data terminal reference number 101 as well as the reference number indicating a host processor 1210. In executing image capture module 1402 with use of portable data terminal 101, it may be desirable, for purposes of enhancing an image quality of captured images, or a consistency of image quality between successively captured images to place portable data terminal 101 in a dark room at the time portable data terminal receives a trigger signal to commence image capture. Portable data terminal 101 may also be placed in a dark room fixture during image capture. A fixture such as the aforementioned dark room fixture may space portable data terminal a fixed distance from a substrate, s, to further enhance image quality and consistency.

Figure 5H:
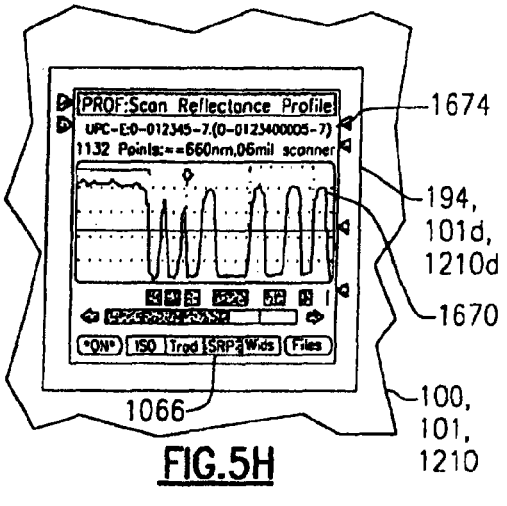
Figure 5I:
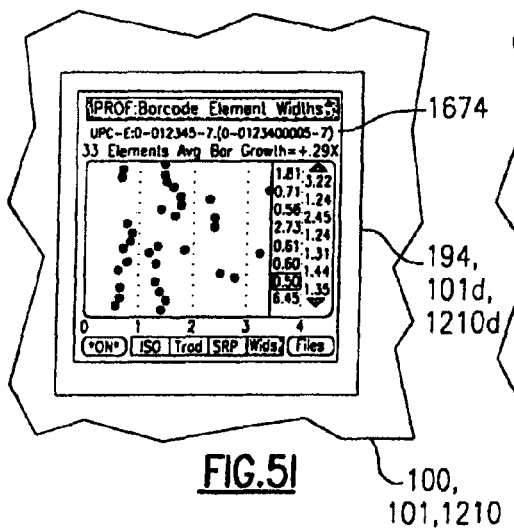
Figure 5J:
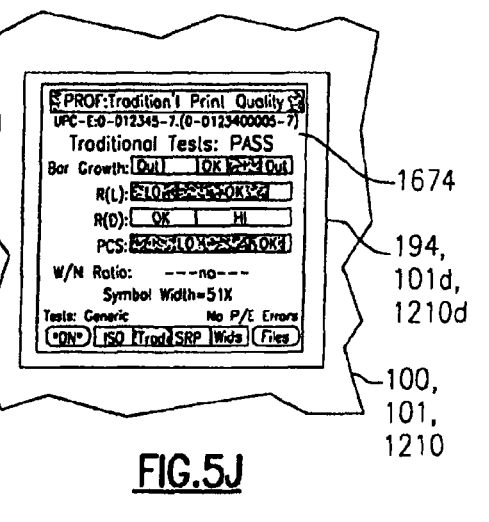
Figure 5K:
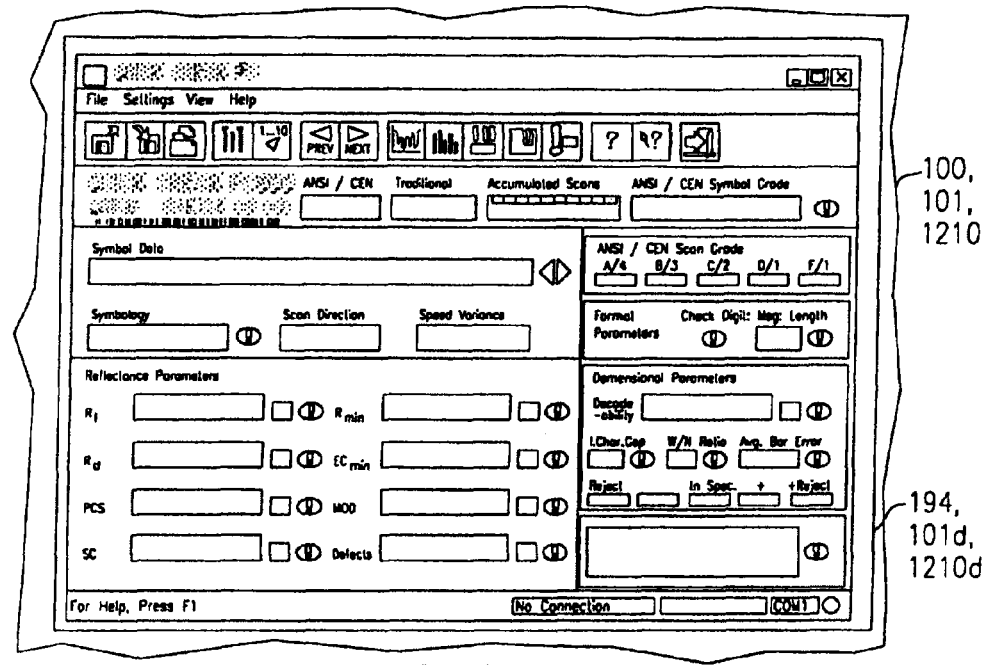
Figure 5L:
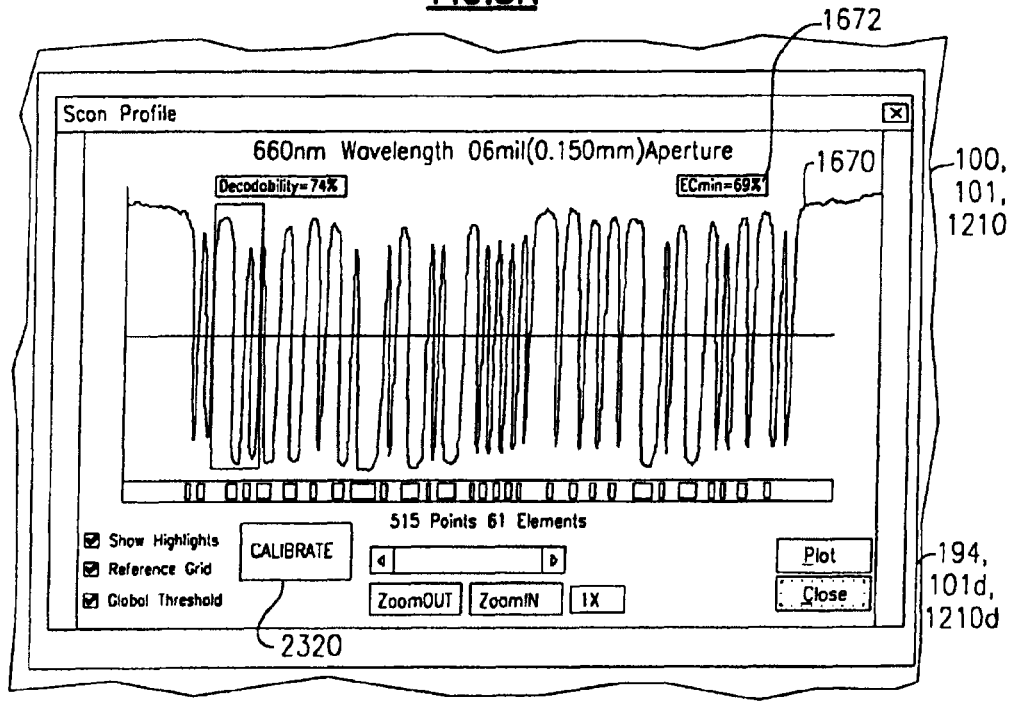
Figure 6E:
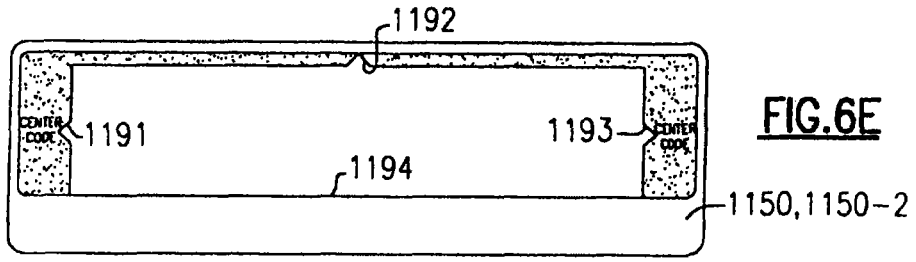
FIGS. 6E-6J illustrate alternative replaceable alignment windows which may be affixed to a housing of a verification device according to the invention.
Figure 6F:
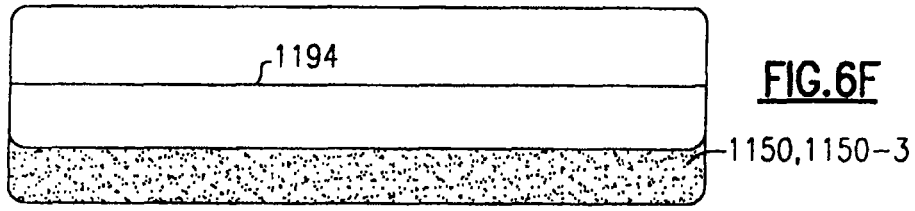
Figure 6G:
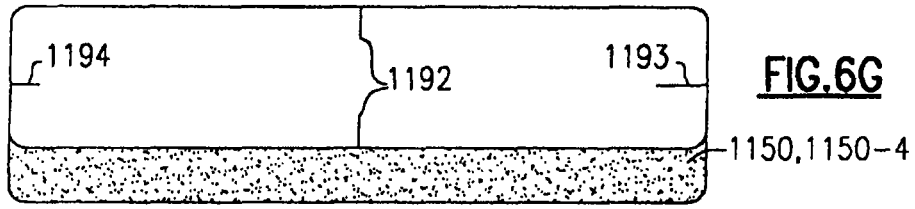
Figure 6H:
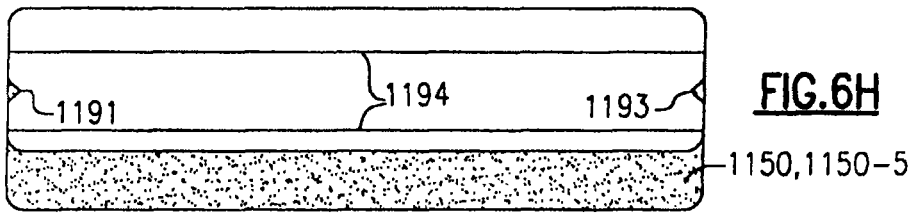
Figure 6I:
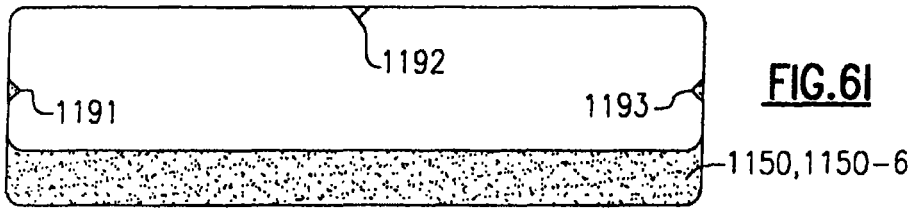
Figure 6J:
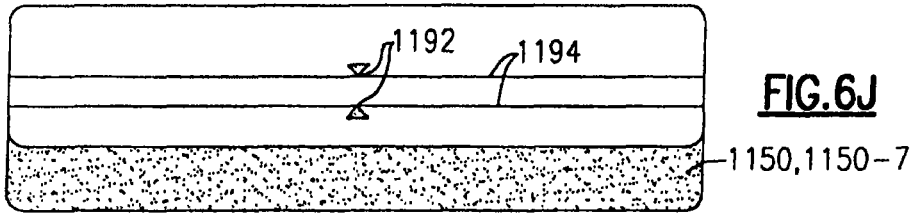

Referring to FIG. 5F another embodiment of the invention is described. In the embodiment of FIG. 5F all of processing modules 1402, 1404, 1406, 1408, 1410, 1422 and 1424 are incorporated into hand held verification device 100 such that housing 1100 having a generally domed configuration for shielding ambient light encapsulates all of modules 1402, 1404, 1406, 1408, 1410, 1422 and 1424. In the embodiment of FIG. 5F, verification device 100 includes a display 194. Referring to assembly views of FIGS. 6A-6D, it is seen that, depending on the size of the display selected it may be necessary to enlarge housing 1100 so that display 194 may be installed in the location indicated without obstructing the path of image forming light rays. Configuring verification device 100 to include display 194 equips device 100 so that device 100 can execute user-interactive waveform analysis module 1424. As explained previously, by execution of user-interactive waveform analysis module 1424 various information respecting bar codes is displayed on a display in response to user input commands. Such user-input commands may include commands to change the format of display and/or information displayed on display. In one mode, device 100 during the execution of module 1424 may display on display 194 a scan reflectance profile 1670 as depicted in FIG. 5H. In another mode of operation as depicted in FIG. 5G, device 100 during execution of module 1424 may display on display 194 various measurement data, such as symbol contrast data 1671, edge contrast data 1672 and modulation data 1673. Device 100 may also display on display 194 decoded output data 1674 as depicted in FIGS. 5G through 5J. In that the hand held housing 1100 depicted in FIG. 5F includes a touch screen 195 associated with display 194, device 100 can be configured so that an operator switches between display formats by contact of a control button with a finger or a stylus. Device 100 can be configured so that the format of display can be switched from that depicted in FIG. 5G to that depicted by FIG. 5H by contacting control button 1066 with a finger or stylus. Because the screen formats of FIGS. 5G-5L may be displayed by host processor 1210 or by portable data terminal 101 configured in accordance with the integration module of FIG. 8A, or by verification device 100 configured in accordance with FIG. 8B, the devices depicted in FIGS. 5G-5L are labeled with the portable data terminal reference number 101 as well as the reference number indicating a host processor 1210, and in addition the reference number indicating verification device 100.

Figure 8C:
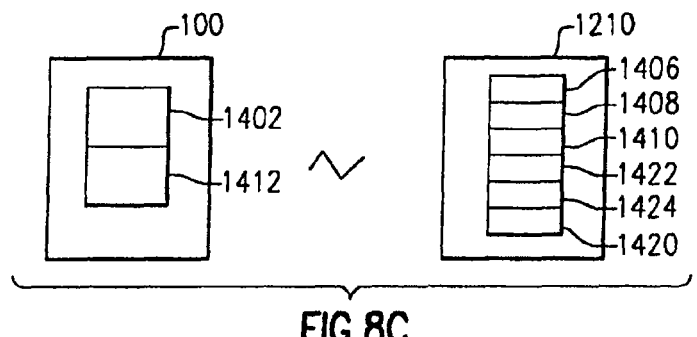

In accordance with the integration diagram of FIG. 8C, processing modules 1402 and 1412 are incorporated in device 100 within housing 1100 while processing modules 1406, 1408, 1410, 1422, 1424 and 1420 are incorporated in spaced apart host processor assembly 1210.

Referring again to features related to the structure of verification device 100 partial assembly views of device 100 are shown in FIGS. 6A-6D. As best seen in FIGS. 6A and 6B base 1114 of housing 1100 supports frame 1152 which extends upwardly from base 1100. At a bottom end of frame 1152 there is supported an electro optical assembly 1156 which carries imaging lens 1070 and image sensor 1060. Base 1114 and frame 1152 support imaging assembly 1140 so that imaging assembly 1140 including image sensor 1060 is positioned to a fixed optical path distance from bar code, B, when device 100 is positioned to perform bar code print quality measurements. At an upper end of frame 1152 there is supported a reflector 1075. Reflector 1075 is carried by reflector mount 1161 having pins 1162 extending therefrom. Pins 1162 in turn are received in pin receivers 1164 of support 1152 so that reflector 1075 is pivotally mounted on support 1152. Reflector 1075 folds imaging axis 1061 (FIG. 2A) so that image forming light rays reflected from a target, T, corresponding to a field of view are directed toward electro optical assembly 1156 incorporates lens 1070 and image sensor chip 1066 (FIG. 2A). A rear surface of frame 1152 supports a printed circuit board 1172 which carries several of the electrical components discussed with reference to FIG. 2A. Referring to further aspects of device 100, device 100 includes set screw 1174 which is positioned operationally relative to reflector 1150. Tightening and loosening set screw 1174 allows precise adjustment of the positioning of reflector 1075 so that the field of view of image sensor 1060 can be precisely adjusted. Device 100 should have at least one source of artificial illumination for use in illuminating bar codes subject to decoding and measuring. In the embodiment of FIGS. 6A through 6D, illumination is provided by LED printed circuit board 1180 which as seen in FIG. 6B includes a plurality of LEDs 1082. LED printed circuit board in the view of FIG. 6A is obscured from view by transparent dust cover 1186. Additional views of components of device that are internal to housing 1100 are provided in the exploded assembly view of FIG. 6K.

Referring to the device 100 bottom view of FIG. 6C, alignment formations 1141, 1142, 1143 are as described earlier herein with respect to FIG. 1C. Alignment member 1150 including alignment formations 1141, 1142, 1143 in the embodiment of FIG. 6B is integrally formed with housing 1100. While alignment formations 1141, 1142, and 1143 in the embodiment of FIGS. 1C and 6B have a discernable thickness and are structural elements, the alignment member 1150 of device 100 for aligning device 100 with bar codes can, include printed matter alignment formations. In FIGS. 6E-6I several alternative alignment members are shown. The alignment members 1150 of FIGS. 6E-6J all comprise transparent (e.g., glass, plastic) inserts having printed matter alignment formations thereon. The printed matter alignment formations may be comprised of e.g., ink, paint, dye, or stickers. Device 100 can be configured so that alignment members 1150 are replaceably received thereon, e.g., with modest strength adhesive. The embodiment of device 100 depicted in FIG. 1B includes a recess 1190 on which a replaceable alignment member, e.g., any one of members 1150-2 through 1150-7 may be received. Replaceable, transparent alignment members 1150-2, 1150-4, 1150-6, and 1150-7 include one or more center alignment formations 1192 which function in the manner of alignment formations 1142, for use horizontally centering of device 100 on a bar code. Replaceable alignment members 1150-2, 1150-4, 1150-5, 1150-6, and 1150-7 have laterally disposed alignment formations 1191 and 1193 which aid an operator in locating device vertically with respect to a vertical center of a bar code. Alignment members 1150-2, 1150-3, 1150-5, 1150-7 include alignment lines 1194. Alignment lines 1194 aid an operator in orienting device 100 so that a field of view of device 100 extends perpendicularly with respect to bars of bar code being subject to decoding and print quality measuring. It is seen that replaceable alignment members 1150-5 and 11500-7 include parallel sets of alignment lines 1194.

In accordance with its major aspects and broadly stated the present invention in one embodiment described is a bar code verification device having an ergonomic form factor characterized by a domed hand held trigger and a viewing window.

The verification device may be disposed in a network that includes a host processor system and other bar code reading devices which may include other bar code verification devices.

Processing circuitry for processing image signals corresponding to printed bar codes may be partially disposed within the hand held verification device and partially disposed within a host processor system spaced apart from and associated with the hand held verification device.

The hand held verification device may be in wireless communication with the host processor system to which it is associated.

The bar code verification system may include signal enhancement modules which interpolate constructed pixel values from actual pixel values and which correct for signal degradation resulting from high frequency spatial sampling.

These and other details and advantages are apparent from the detailed description of the preferred embodiment.

While the present invention has been particularly shown and described with reference to the preferred mode as illustrated in the drawings, it will be understood by one skilled in the art that various changes in detail may be effected therein without departing from the spirit and scope of the invention as defined by the claims.

We claim:

1. A device for verification of a bar code disposed on a horizontal substrate, said device comprising:
   (A) an imaging assembly including a solid state image sensor;
   (B) a housing encapsulating a component of said imaging assembly, said housing having a plurality of surfaces that extend generally upward from said substrate when said device is positioned in a position to measure print quality of said bar code;
   (C) an illumination assembly at least partially disposed in said housing projecting illumination onto said substrate;
   (D) an image capture module configured to capture at least one frame of image data corresponding to a bar code symbol;
   (E) a bar code quality measurement module configured to determine at least one of: a value of contrast of said bar code symbol, a value of edge contrast of said bar code symbol, a value of modulation of said bar code symbol;
   (F) wherein said device is configured to automatically execute said image capture module and said bar code print quality measurement module;
   (G) an aperture formed on said housing, said aperture being formed on said housing in such position that an operator can view said bar code through said aperture when said device is positioned in said position to measure print quality of said bar code; and (G) at least one alignment formation for aiding alignment of said device relative to said bar code, said at least one alignment formation formed at a bottom of said device, said at least one alignment formation and said aperture being positioned so that an operator can view said at least one alignment formation through said aperture when said device is positioned in said position to measure print quality of said bar code.

2. The device of claim 1, wherein said aperture receives a light transmissive window.

3. The device of claim 1, wherein said aperture receives a manually removable opaque window.

4. The device of claim 1, wherein said at least one alignment formation is formed on said housing.

5. The device of claim 1, wherein said at least one alignment formation is formed on a replaceable alignment member.

6. The device of claim 1, wherein said at least one alignment formation includes a center alignment formation for aiding horizontal centering of said device on said bar code.

7. The device of claim 1, wherein said at least one alignment formation includes a pair of laterally disposed alignment formations for aiding vertical centering of said device on a bar code.

8. The device of claim 1, wherein said at least one alignment formation is provided by an alignment light formed on a transparent member.

* * * * *